US007829570B2

(12) United States Patent
Hirst et al.

(10) Patent No.: US 7,829,570 B2
(45) Date of Patent: Nov. 9, 2010

(54) SUBSTITUTED 4-AMINO ISOXAZOLO[5,4-D]PYRIMIDINES AS KINASE INHIBITORS

(75) Inventors: Gavin C. Hirst, San Diego, CA (US); Andrew Burchat, Shrewsbury, MA (US); Neil Wishart, Jefferson, MA (US); David J. Calderwood, Framingham, MA (US); Michael R. Michaelides, Libertyville, IL (US); Zhiqin Ji, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 141 days.

(21) Appl. No.: 12/315,416

(22) Filed: Dec. 3, 2008

(65) Prior Publication Data

US 2010/0041676 A1    Feb. 18, 2010

Related U.S. Application Data

(62) Division of application No. 10/394,965, filed on Mar. 21, 2003, now abandoned.

(60) Provisional application No. 60/366,422, filed on Mar. 21, 2002.

(51) Int. Cl.
*C07D 498/04* (2006.01)
*A61K 31/424* (2006.01)
*A61K 31/519* (2006.01)
*A61P 35/00* (2006.01)
*A61P 9/00* (2006.01)
*A61P 37/06* (2006.01)

(52) U.S. Cl. .................... 514/260.1; 544/255
(58) Field of Classification Search ................ 544/255; 514/260.1
See application file for complete search history.

(56) References Cited

U.S. PATENT DOCUMENTS

2003/0199525 A1    10/2003    Hirst et al.

OTHER PUBLICATIONS

Stacker, S.A. et al, Mutations in the V3 Domain of the Cysteine-Knot Motif of Mouse . . . ,(1998), Angiogenesis and Cancer Conference Center, Amer. Assoc. Cancer Res.
Takano et al, Inhibition of Angiogenesis by a Novel Diaminoanthraquinone that Inhibits Protein Kinases C., (1993), Mol. Bio. Cell, vol. 4, pp. 358A.
Taylor E.C. et al, The Synthesis of 4-Aminoisoxazolo [5.4-d] pyrimidines, (1964) Journal of Organic Chemistry, vol. 29(8), pp. 2116-2120.
Terman et al, Identification of a New Endothelial Cell Growth Factor Receptor Tyrosine Kinase, (1991), Oncogene, vol. 6, pp. 1677-1683.
Terman et al, Identification of the KDR Tyrosine Kinase as a Receptor for Vascular . . . , (1992), Biochem. Biophys. Res. Comm., vol. 187(3), pp. 1579-1586.
't Hart et al,Evaluating the validity of animal models for research into therapies for immune-based disorders, (2004) Drug Discovery Today, vol. 9(12), pp. 517-524.
Ulrich et al., Signal Transduction by Receptors with Tyrosine Kinase Activity, (1990), Cell, vol. 61, pp. 203-212.
Williams, Factors regulating the Expression of Vascular Permeability/Vascular Endothelial Growth Factory by Human Vascular Tissues, (1997) Diabetelogia, vol. 40, pp. S118-S120.
Witzenbichler et al, Vascular Endothelial Growth Factor-C (VEGF-C/VEGF-2) Promotes Angiogenesis in the Setting of Tissue . . . , (1998), Am. J. Pathol., vol. 153(2), pp. 381-394.
Wolff, Burger's Medicinal Chemistry, 5th Edition, Part 1, (1995), pp. 975-977.
Wright et al, inhibition of Angiogenesis In Vitro and In Ovo with an Inhibitor, of Cellular Protein Kinases, MDL 27032, (1992), J. Cellular Phys., vol. 152, pp. 448-457.
Yang et al., Expression and Function of Murine Receptor Tyrosine Linases, TIE and TEK, in Hematopoietic Stem Cells, (1997), Blood, vol. 89(12), pp. 4317-4326.
Yarden et al., Growth Factor Receptor Tyrosine Kinases, (1988), Ann. Rev. Biochem., vol. 57, pp. 443-478.
Achen et al, Vascular Endothelial Growth Factor D (VEGF-D) is a Ligand for the Tyrosine . . . , (1998), Proc. Natl. Acad. Sci. USA, vol. 95(2), pp. 548-553.
4-Anilinoquinazoline Derivatives, (1998), Expert Opin. Ther. Pat., vol. 8(4), pp. 475-478.
Belenkii, L.I. et al, Synthesis of Hheterocycles Based on products of Additon of Polyhaloalkanes to Unsaturated Systems . . . , (1994), Chemical Abstracts, vol. 120(13), pp. 1175.
Brickell et al., The p60 Family of Protein -Tyrosine Kinases: Structure, Regulation, and Function, (1992), Critical Reviews in Oncogenesis, vol. 3(4), pp. 401-446.
Brown et al, Vascular Permeability Factor/Vascular Endothelial . . . , (1997), Regulation of Angiogenesis (ed. L.D. Goldberg and E.M. Rosen), pp. 233-269.
Buchdunger et al., Selective inhibition of the platelet-derived growth factor signa; transduction pathway by a protein-tyrosine kinase inhibitor of the 2-phenyloaminopyrimidine class, (1995), Proc. Natl. Acad. Sci. USA, vol. 92, pp. 2558-2562.

(Continued)

*Primary Examiner*—James O Wilson
*Assistant Examiner*—Susanna Moore
(74) *Attorney, Agent, or Firm*—Gayle B. O'Brien; Kenneth P. Lwicker

(57) ABSTRACT

The present application is directed to compounds of the formula (I)

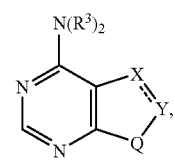

wherein the substituents are as defined herein, which are useful as kinase inhibitors.

7 Claims, No Drawings

OTHER PUBLICATIONS

Connolly et al, Human Vascular Permeability, (1989), J. Biol. Chem., vol. 264, pp. 20017-20024.

Courtneidge et al., Protein tyrosine kinases, with emphasis on the Src family, (1994), Seminars in Cancer Biology, vol. 5, pp. 239-246.

Cowburn, Peptide Recognition by PTB and PDZ Domains, (1997), Currr. Opin. Struct. Biol., vol. 7(6), pp. 835-838.

Cullinan-Bove et al., Vascular Endothelial Growth Factor/Vascular Permeability Factor Expression in the Rat Uterus: Rapid Stimulation by Estrogen . . . , (1993), Endocrinology, vol. 133(2), pp. 829-837.

De Vries et al, The fms-Like Tyrosine Kinase, a Receptor for Vascular Endothelial Growth Factor, (1992), Science, vol. 255, pp. 989-991.

Draetta, cdc2 activation: the interplay of cyclin binding and Thr161 phosphorylation, (1993), Trends in Cell Biology, vol. 3, pp. 287-289.

Ducommun et al., cdc2 phosphorylation is required for its interaction with cyclin, (1991), The EMBO Journal, vol. 10 (11), pp. 3311-3319.

Fantl et al, Distinct Phosphotyrosines on a Growth Factor Receptor Bind to Specific Molecules that Mediate Different Signaling Pathways, (1992), Cell, vol. 69, pp. 413-423.

Ferrara et al, The Vascular Endothelial Growth Factor Family of Poly peptides, (1991), J. Cell. Biochem., vol. 47, pp. 211-218.

Ferrara et al, The Biology of Vascular Endothelial Growth Factor, (1997), Endocrine Reviews, vol. 18(1), pp. 4-25.

Isner et al., Angiogenesis and vsculogenesis as therapeutic strategies for postnatal neovscukarization, (1999), The Journal of Clinical Investigation, vol. 103(9), 1231-1236.

Jakeman et al, Developmental Expression of Binding Sites and Messenger Ribnucleic Acid for Vasular Endothelial . . . , (1993), Endocrinology, vol. 133(2), pp. 848-859.

Jellinek et al, Inhibition of Receptor Binding by High-Affinity RNA Ligands to Vascular Endothelial Growth Factor, (1994), Biochemistry, vol. 33, pp. 10450-10456.

Kendall & Thomas, Inhibition of Vascular Endothelial Cell Growth Factor Activity by and Endogenously Encoded . . . , (1994), Proc. Natl. Acad. Sci., vol. 90, pp. 10705-10709.

Kim et al, Inhibition of Vascular Endothelial Growth Factor-Induced Angiogenesis Suppresses Tumor Growth in vivo, (1993), Nature, vol. 362, pp. 841-844.

Kinsella et al, protein Kinases C Regulates Endothelial Cell Tube Formation on Basement Membrane Matrix, Matrige, (1992), Exp. Cell. Res., vol. 199, pp. 56-62.

Klagsbrun et al., Vascular Endothelial Growth Factor and its Receptors, (1996), Cytokine & Growth Factor Reviews, vol. 7(3), pp. 259-270.

Koch et al, SH2 and SH3 Domains: Elements that Control Interactions of Cytoplasmic Signaling Proteins, (1991), Science, vol. 252, pp. 668-678.

Kolch et al, Regulation of the Expression of the VEFG/VPS and its Receptors: Rile in Tumor Angiogenesis, (1995), Breast Cancer Research and Treatment, vol. 36, pp. 139-155.

Korpelainen et al., Signaling Angiogenesis and Lymphangiogenesis, (1998), Curr. Opin. Cell Biol., vol. 10, pp. 159-164.

Lees, Cyclin dependent kinase regulation, (1995), Current Opinion in Cell Biology, vol. 7, pp. 773-780.

Lymboussaki et al, Expression of the Vascular Endothelial Growth Factor C Receptor VEGFR-3 in Lymphatic . . . , (1998), Am. J. Pathol., vol. 153(2), pp. 381-394.

Maglione et al, Two Alternative mRNAs Coding for the Angiogenic Factor, Placenta Growth Factor (PIGF), are Transcribed from . . . , (1993), Oncogene, vol. 8, pp. 925-931.

Mariani et al, Inhibition of Angiogenesis by FCE 26806, a Potent Tyrosine Kinase inhibitor, (1994), Proc. Am. Assoc. Cancer Res., vol. 35, pp. 2268.

Matthews et al, A Receptor Tyrosine Kinase cDNA Isolated from a Population of Enriched Primitive Hematopoietic . . . , (1991), Proc. Natl. Acad. Sci. USA, vol. 88, pp. 9026-9030.

Matsushime et al., D-Type Cyclin-Dependent Kinase Activity in Mammalian Cells, (1994), Molecular and Cellular Biology, vol. 14(3), pp. 2066-2076.

Mayo Clinic Staff, Rheumatoid Arthritis, Retrieved from internet Nov. 4, 2004 <http://www.mayoclinic.com/invoke.cfm?id=DS00020&dsection=1>.

Meyer et al, A Novel Vascular Endothelial Growth Factor Encoded by Orf Virus, VEFG-E, Mediates Angiogenesis . . . , (1999), EMBO J., vol. 18(2), pp. 363-374.

Migdal et al, Neuropilin-1 is a Placenta Growth Factor-2 Receptor, (1998), J. Biol. Chem., vol. 273(35), pp. 22272-22278.

Millauer et al, High Affinity VEGF Binding and Developmental Expression Suggest Flk-1 as a Major Regulator of Vasculo genesis . . . , (1993), Cell, vol. 72, pp. 835-846.

Mustonen et al., Endothelial receptor Tyrosine Kinases Involved in Angiogenesis, (1995), J. Cell Biol., vol. 129(4), pp. 895-898.

Noble et al, Protein Kinase Inhibitors: Insights into Drug Design from Structure, (2004), Science, vol. 303, pp. 1800-1805.

Oelrichs et al, NYK/FLK-1: a Putative Receptor Protein Tyrosine Kinase Isolated From E10 Embryonic Neuroepithelium is Expressed in . . . , Oncogene, vol. 8(1), pp. 11-18, (1993).

Ogawa et al, A Novel Type of Vascular Endothelial Growth Factor, VEGF-E (NZ-7 VEGF), Preferentialy Utilizes . . . , (1998), J. Biol. Chem., vol. 273(47), pp. 3127-31282.

Olofsson et al, Vascular Endothelial Growth Factor B (VEGF-B) Binds to VEGF Receptor-1 . . . (1998), Proc. Natl. Acad. Sci. USA, vol. 95; pp. 11709-11714.

Park et al, Placenta Growth Factor, (1994), J. Biol. Chem., vol. 269, pp. 25646-25654.

Rajagopalan et al, Synthesis of 4-Hydroxy-, 4-Chloro-, 4-Amino- and 4-Substituted Aminoisoxazolo, (1967), Tetrahedron, vol. 23, pp. 3541-3543.

Rao et al, Synthesis of Triple Helix Forming Oligonucleotides containing 2'-deoxyformycin A., (1994) Chemical Abstracts, vol. 121(13), pp. 1073.

Ristimaki et al, Proinflammatory Cytokines Regulate Expression of the Lymphatic Endothelial . . . , (1998), J. Biol. Chem., vol. 273(14) pp. 8413-8418.

Schlessinger et al., Growth Factor Signaling by Receptor Tyrosine Kinases, (1992), Neuron, vol. 9, pp. 383-391.

Shibuya et al, Nucleotide Sequence and Expression of a Novel Human Receptor-Type Tyrosine Kinase Gene (flt) Closely Related to the . . . , (1990), Oncogene, vol. 5, pp. 519-524.

Shishoo, C.J. et al, Reaction of Nitriles under Acidic Conditions . . . , (1990), Journal of Heterocyclic Chemistry, vol. 27, pp. 119-126.

Shoelson, SH2 and PTB Domain Interactions in Tyrosine Kinase Signal Trasduction, (1997), Curr. Opin. Chem. Biol., vol. 1(2), pp. 227-234.

Songyang et al, Mol. Cell. Biol., (1994), vol. 14(4), pp. 2777-2785.

SUBSTITUTED 4-AMINO ISOXAZOLO[5,4-D]PYRIMIDINES AS KINASE INHIBITORS

CROSS REFERENCE TO RELATED APPLICATION

This application is a divisional of U.S. Ser. No. 10/394,965 filed Mar. 21, 2003 now abandoned and claims priority to U.S. Provisional Application Ser. No. 60/366,422 filed on Mar. 21, 2002.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383-391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schiessinger and Ullrich, 1992, *Neuron* 9:1-20.

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413-423; Songyang et al., 1994, *Mol. Cell. Biol.* 14:2777-2785; Songyang et al., 1993, *Cell* 72:767-778; and Koch et al., 1991, *Science* 252:668-678; Shoelson, *Curr. Opin. Chem. Biol.* (1997), 1(2), 227-234; Cowburn, *Curr. Opin. Struct. Biol.* (1997), 7(6), 835-838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767-778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767-778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, TIE-2 and c-Met, and growth factors that bind thereto, have been suggested to play a role in angiogenesis, although some may promote angiogenesis indirectly (Mustonen and Alitalo, *J. Cell Biol.* 129:895-898, 1995). One such receptor tyrosine kinase, known as Afetal liver kinase 1≅(FLK-1), is a member of the type III subclass of RTKs. An alternative designation for human FLK-1 is Akinase insert domain-containing receptor≅(KDR) (Terman et al., *Oncogene* 6:1677-83, 1991). Another alternative designation for FLK-1/KDR is Avascular endothelial cell growth factor receptor 2≅(VEGFR-2) since it binds VEGF with high affinity. The murine version of FLK-1/VEGFR-2 has also been called NYK (Oelrichs et al, *Oncogene* 8(1): 11-15, 1993). DNAs encoding mouse, rat and human FLK-1 have been isolated, and the nucleotide and encoded amino acid sequences reported (Matthews et al., *Proc. Natl. Acad. Sci.*

USA, 88:9026-30, 1991; Terman et al., 1991, supra; Terman et al., *Biochem. Biophys. Res. Comm.* 187:1579-86, 1992; Sarzani et al., supra; and Millauer et al., *Cell* 72:835-846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated Afins-like tyrosine kinase-1≅(Flt-1) is related to FLK-1/KDR (DeVries et al. *Science* 255; 989-991, 1992; Shibuya et al., *Oncogene* 5:519-524, 1990). An alternative designation for Flt-1 is Avascular endothelial cell growth factor receptor 1≅(VEGFR-1). To date, members of the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D=Amore, *Cytokine & Growth Factor Reviews* 7: 259-270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in monocytes, osteoclasts, and osteoblasts, as well as in adult tissues such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., *Endocrinology* 133: 848-859, 1993; Kolch et al., *Breast Cancer Research and Treatment* 36: 139-155, 1995; Ferrara et al., *Endocrine Reviews* 18(1); 4-25, 1997; Ferrara et al., *Regulation of Angiogenesis* (ed. L. D. Goldberg and E. M. Rosen), 209-232, 1997). In addition, VEGF has been implicated in the control and enhancement of vascular permeability (Connolly, et al., *J. Biol. Chem.* 264: 20017-20024, 1989; Brown et al., *Regulation of Angiogenesis* (ed. L. D. Goldberg and E. M. Rosen), 233-269, 1997). Different forms of VEGF arising from alternative splicing of mRNA have been reported, including the four species described by Ferrara et al. (*J. Cell. Biochem.* 47:211-218, 1991). Both secreted and predominantly cell-associated species of VEGF have been identified by Ferrara et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.*, 159-164, 1998 and references cited therein).

Placenta growth factor (PlGF) has an amino acid sequence that exhibits significant homology to the VEGF sequence (Park et al., *J. Biol. Chem.* 269:25646-54, 1994; Maglione et al. *Oncogene* 8:925-31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al, *J. Biol. Chem.* 273 (35): 22272-22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper et al, *Proc. Natl. Acad. Sci. U.S.A.* (1998), 95(20): 11709-11714).

VEGF-C was originally cloned as a ligand for VEGFR-3/Flt4 which is primarily expressed by lymphatic endothelial cells. In its fully processed form, VEGF-C can also bind KDRNEGFR-2 and stimulate proliferation and migration of endothelial cells in vitro and angiogenesis in in vivo models (Lymboussaki et al, *Am. J. Pathol.* (1998), 153(2): 395-403; Witzenbichler et al, *Am. J. Pathol.* (1998), 153(2), 381-394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14), 8413-8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S.A.* (1998), 95(2), 548-553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

There has been recently reported a virally encoded, novel type of vascular endothelial growth factor, VEGF-E (NZ-7 VEGF), which preferentially utilizes KDR/Flk-1 receptor and carries a potent mitotic activity without heparin-binding domain (Meyer et al, *EMBO J.* (1999), 18(2), 363-374; Ogawa et al, *J. Biol. Chem.* (1998), 273(47), 31273-31282). VEGF-E sequences possess 25% homology to mammalian VEGF and are encoded by the parapoxvirus Orf virus (OV). This parapoxvirus that affects sheep and goats and occasionally, humans, to generate lesions with angiogenesis. VEGF-E is a dimer of about 20 kDa with no basic domain nor affinity for heparin, but has the characteristic cysteine knot motif present in all mammalian VEGFs, and was surprisingly found to possess potency and bioactivities similar to the heparin-binding VEGF 165 isoform of VEGF-A, i.e. both factors stimulate the release of tissue factor (TF), the proliferation, chemotaxis and sprouting of cultured vascular endothelial cells in vitro and angiogenesis in vivo. Like VEGF165, VEGF-E was found to bind with high affinity to VEGF receptor-2 (KDR) resulting in receptor autophosphorylation and a biphasic rise in free intracellular Ca2+ concentrations, while in contrast to VEGF165, VEGF-E did not bind to VEGF receptor-1 (Flt-1).

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., AAngiogenesis and Cancer≅Conference, Amer. Assoc. Cancer Res., January 1998, Orlando, Fla.; Williams, *Diabetelogia* 40: S118-120 (1997)). Until now, no direct evidence for the essential role of KDR in VEGF-mediated vascular hyperpermeability has been disclosed.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bolen, 1993, *Oncogene* 8:2025-2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKS. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (Application No. WO 94/10202; Kendall & Thomas, 1994, *Proc. Natl. Acad. Sci.* 90:10705-09; Kim et al., 1993, *Nature* 362:841-844), RNA ligands (Jellinek, et al., *Biochemistry* 33:10450-56; Takano, et al., 1993, *Mol. Bio. Cell* 4:358A; Kinsella, et al. 1992, *Exp. Cell Res.* 199:56-62; Wright, et al., 1992, *J. Cellular Phys.* 152:448-57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475-478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is Also Known as cdk1)

Cdc2/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors could suppress proliferation and may restore the normal control of cell cycle progression.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for antiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention provides a compound of formula I,

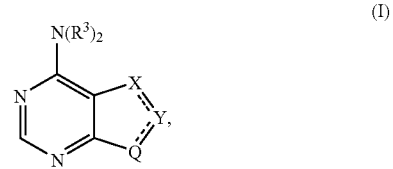

the racemic-diastereomeric mixtures, optical isomers, pharmaceutically-acceptable salts, prodrugs or biologically active metabolites thereof, wherein the dotted line in the structure of formula (I) represents an optional double bond;

X is $CR^1$ or $NR^1$; Y is O, $CR_q$ or N; Q is N, $NR^2$ or O;

$R^3$ for each occurrence is independently hydrogen, hydroxy, substituted or unsubstituted alkyl or substituted or unsubstituted alkoxy;

when X is $CR^1$, Y is $CR_q$, Q is O and there is a double bond between X and Y; or when X is $CR^1$, Y is N, Q is O and there is a double bond between X and Y; or when X is $CR^1$, Y is O, Q is N and there is a double bond between Q and the pyrimidinyl ring, then $R^1$ is

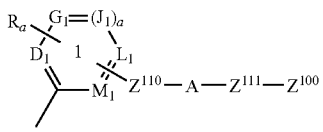

where $Z^{100}$ is nitro, optionally substituted amino,

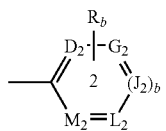

or a group optionally substituted with $R_b$ selected from the group consisting of cycloalkyl, naphthyl, tetrahydronaphthyl, benzothienyl, furanyl, thienyl, benzoxazolyl, benzothiazolyl,

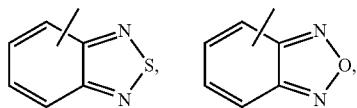

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, oxazolyl, isothiazolyl, oxadiazolyl, thiadiazolyl, indolinyl, indazolyl, benzoisothiazolyl, pyrido-oxazolyl, pyrido-thiazolyl, pyrimido-oxazolyl, pyrimido-thiazolyl and benzimidazolyl;

when a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or when a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N;

when b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or when b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N;

$R_a$ and $R_b$ each represent one or more substituents and are for each occurrence independently selected from the group consisting of hydrogen, halogen, —CN, —$NO_2$, —C(O)OH, —C(O)H, —OH, —C(O)O-alkyl, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{201}$, $R_c$, $CH_2OR_c$, tetrazolyl, trifluoromethylcarbonylamino, trifluoromethylsulfonamido, and an optionally substituted group selected from the group consisting of carboxamido, alkyl, alkoxy, aryl, alkenyl, aryloxy, heteroaryloxy, arylalkyl, alkynyl, amino, aminoallyl, amido groups, heteroarylthio and arylthio;

$Z^{105}$ for each occurrence is independently a covalent bond or ($C_1$-$C_6$);

$Z^{200}$ for each occurrence is independently an optionally substituted ($C_1$-$C_6$), optionally substituted phenyl, or optionally substituted —($C_1$-$C_6$)-phenyl;

$R_c$ for each occurrence is independently hydrogen, optionally substituted alkyl, optionally substituted aryl, —$CH_2$—$NR_dR_e$, —W—($CH_2$), —$NR_dR_e$, —W—($CH_2$)$_t$—Oalkyl, —W—($CH_2$), —S-alkyl or —W—($CH_2$)$_t$—OH;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), S(O)$_2$, or $NR_f$;

$R_f$ for each occurrence is independently H or alkyl;

$Z^{110}$ is a covalent bond, or an optionally substituted ($C_1$-$C_6$) which is optionally substituted with one or more substituents selected from the group consisting of alkyl, CN, OH, halogen, $NO_2$, COOH, optionally substituted amino and optionally substituted phenyl;

$Z^{111}$ is a covalent bond, an optionally substituted ($C_1$-$C_6$) or an optionally substituted —($CH_2$)$_n$-cycloalkyl-($CH_2$)$_n$—; where the optionally substituted groups are optionally substituted with one or more substituents selected from the group consisting of alkyl, CN, OH, halogen, $NO_2$, COOH, optionally substituted amino and optionally substituted phenyl;

or $R^1$ is a substituted or unsubstituted carbocyclic or heterocyclic ring fused with ring 2;

A is a covalent bond, —O—; —S—; —S(O)$_p$—; —N(R)—; —N(C(O)OR)—; —N(C(O)R)—; —N(SO$_2$R)—; —$CH_2$O—; —$CH_2$S—; —$CH_2$N(R)—; —CH(NR)—; —$CH_2$N(C(O)R))—; —$CH_2$N(C(O)OR)—; —$CH_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR); —CH═CH—; —C(═NOR)—; —C(O)—; —CH(OR)—; —C(O)N(R)—; —N(R)C(O)—; —N(R)S(O)$_p$—; —OC(O)N(R)—; —N(R)—C(O)—($CH_2$)$_n$—N(R)—, —N(R)C(O)O—; —N(R)—($CH_2$)$_{n+1}$—C(O)—, —S(O)$_p$N(R)—; —O—($CR_2$)$_{n+1}$—C(O)—, —O—($CR_2$)$_{n+1}$—O—, —N(C(O)R)S(O)$_p$—; —N(R)S(O)$_p$N(R)—; —N(R)—C(O)—($CH_2$)$_n$—O—, —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_g$)O—; —N(R)P(OR$_g$)—; —N(R)P(O)(OR$_g$)O—; —N(R)P(O)(OR$_g$)—; —N(C(O)R)P(OR$_g$)O—; —N(C(O)R)P(OR$_g$—; —N(C(O)R)P(O)(OR$_g$)O—, or —N(C(O)R)P(OR$_g$)—;

p is 1 or 2;

R for each occurrence is independently H, optionally substituted alkyl, optionally substituted arylalkyl or optionally substituted aryl;

$R_g$ for each occurrence is independently H, or an optionally substituted group selected from the group consisting of alkyl, arylalkyl, cycloalkyl and aryl;

or R, $R_g$, the nitrogen atom and the phosphorus atom, together form a five- or six-membered heterocyclic ring when R and $R_g$ are in a phosphorus containing group; or A is $NRSO_2$ and R, $R_a$ and the nitrogen atom together form an optionally substituted five or -six-membered heterocyclic ring fused to ring 1;

n for each occurrence is independently an integer from 0 to 6;

$R_q$ is selected from the group consisting of hydrogen, alkoxyalkyl, alkyl, optionally substituted arylalkyl, optionally substituted cycloalkyl, optionally substituted cycloalkylalkyl, optionally substituted heteroaralkyl, optionally substituted (heterocycloalkyl)alkyl, and halo; wherein the arylalkyl, the cycloalkyl, the cycloalkylalkyl, the heteroaralkyl, and the (heterocycloalkyl)alkyl are each optionally substituted with one, two, three, four, or five substituents independently selected from the group consisting of alkoxy, alkoxyalkyl, alkyl, cyano, halo, haloalkyl, hydroxy, hydroxyalkyl and nitro; or when X is $NR^1$ and $R^3$ are each H, then Y is N, Q is $CR^2$, there is a double bond between Y and Q, and $R^1$ is

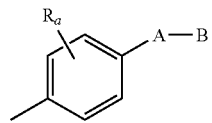

wherein $R_a$ is H or —OMe;
A is —NH—CO—, —NH—$SO_2$—, —NH—C(O)O— or —NH—C(O)—NH—;
B is N-methyl-indol-2-yl, (fluoro)(trifluoromethyl)phenyl, phenyl or benzyl;
$R^2$ is H, 4-piperidinyl,

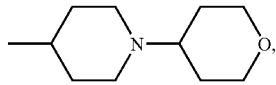

N-ethylpiperidin-4-yl or

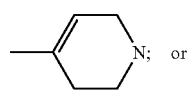

when X is $CR^1$ and one of $R^3$ is not H, then Y is N, Q is $NR^2$, there is a double bond between X and Y, and $R^1$ is

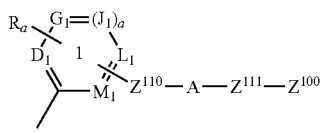

where $Z^{100}$ is nitro, optionally substituted amino,

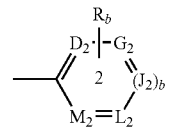

or a group optionally substituted with $R_b$ selected from the group consisting of cycloalkyl, naphthyl, tetrahydronaphthyl, benzothienyl, furanyl, thienyl, benzoxazolyl, benzothiazolyl,

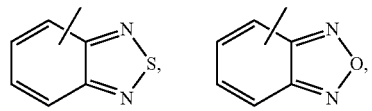

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, oxazolyl, isothiazolyl, oxadiazolyl, thiadiazolyl, indolinyl, indazolyl, benzoisothiazolyl, pyrido-oxazolyl, pyrido-thiazolyl, pyrimido-oxazolyl, pyrimido-thiazolyl and benzimidazolyl;

when a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or when a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N;

when b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or when b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N;

$R_a$ and $R_b$ each represent one or more substituents and are for each occurrence independently selected from the group consisting of hydrogen, halogen, —CN, —$NO_2$, —C(O)OH, —C(O)H, —OH, —C(O)O-alkyl, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{200}$, $R_b$, $CH_2OR_b$, tetrazolyl, trifluoromethylcarbonylamino, trifluoromethylsulfonamido, and an optionally substituted group selected from the group consisting of carboxamido, alkyl, alkoxy, aryl, alkenyl, aryloxy, heteroaryloxy, arylalkyl, alkynyl, amino, aminoalkyl, amido groups, heteroarylthio and arylthio;

$Z^{105}$ for each occurrence is independently a covalent bond or ($C_1$-$C_6$);

$Z^{200}$ for each occurrence is independently an optionally substituted ($C_1$-$C_6$), optionally substituted phenyl, or optionally substituted —($C_1$-$C_6$)-phenyl;

$R_c$ for each occurrence is independently hydrogen, optionally substituted alkyl, optionally substituted aryl, —$CH_2$—$NR_dR_e$, —W—$(CH_2)_t$—$NR_dR_e$, —W—$(CH_2)_t$—Oalkyl, —W—$(CH_2)_t$—S-alkyl or —W—$(CH_2)$, —OH;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), $S(O)_2$, or $NR_f$;

$R_f$ for each occurrence is independently H or alkyl;

$Z^{110}$ is a covalent bond, or an optionally substituted ($C_1$-$C_6$) which is optionally substituted with one or more substituents selected from the group consisting of alkyl, CN, OH, halogen, $NO_2$, COOH, optionally substituted amino and optionally substituted phenyl;

$Z^{111}$ is a covalent bond, an optionally substituted ($C_1$-$C_6$) or an optionally substituted —$(CH_2)_n$-cycloalkyl-$(CH_2)_n$—; where the optionally substituted groups are optionally substituted with one or more substituents selected from the group consisting of alkyl, CN, OH, halogen, $NO_2$, COOH, optionally substituted amino and optionally substituted phenyl;

or $R^1$ is a substituted or unsubstituted carbocyclic or heterocyclic ring fused with ring 2;

A is a covalent bond, —O—; —S—; —S(O)$_p$—; —N(R)—; —N(C(O)OR)—; —N(C(O)R)—; —N(SO$_2$R)—; —CH$_2$O—; —CH$_2$S—; —CH$_2$N(R)—; —CH(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR); —CH=CH—; —C(=NOR)—; —C(O)—; —CH(OR)—; —C(O)N(R)—; —N(R)C(O)—; —N(R)S(O)$_p$—; —OC(O)N(R)—; —N(R)—C(O)—(CH$_2$)$_n$—N(R)—, —N(R)C(O)O—; —N(R)—(CH$_2$)$_{n+1}$—C(O)—, —S(O)$_p$N(R)—; —O—(CR$_2$)$_{n+1}$—C(O)—, —O—(CR$_2$)$_{n+1}$—O—, —N(C(O)R)S(O)$_p$—; —N(R)S(O)$_p$N(R)—; —N(R)—C(O)—(CH$_2$)$_p$—O—, —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_g$)O—; —N(R)P(OR$_g$)—; —N(R)P(O)(OR$_g$)O—; —N(R)P(O)(OR$_g$)—; —N(C(O)R)P(OR$_g$)O—; —N(C(O)R)P(OR$_g$)—; —N(C(O)R)P(O)(OR$_g$)O—, or —N(C(O)R)P(OR$_g$)—;

p is 1 or 2;

R for each occurrence is independently H, optionally substituted alkyl, optionally substituted arylalkyl or optionally substituted aryl;

$R_g$ for each occurrence is independently H, or an optionally substituted group selected from the group consisting of alkyl, arylalkyl, cycloalkyl and aryl;

or R, $R_g$, the nitrogen atom and the phosphorus atom, together form a five- or six-membered heterocyclic ring when R and $R_g$ are in a phosphorus containing group; or A is $NRSO_2$ and R, $R_a$ and the nitrogen atom together form an optionally substituted five or -six-membered heterocyclic ring fused to ring 1;

$R^2$ is —$Z^{101}$—$Z^{102}$;

$Z^{101}$ is a covalent bond, —($C_1$-$C_6$)—, —($C_1$-$C_6$)—O—, —($C_1$-$C_6$)—C(O)—, —($C_1$-$C_6$)—C(O)O—, —($C_1$-$C_6$)—C(O)—NH—, —($C_1$-$C_6$)—C(O)—N(($C_1$-$C_6$))— or an optionally substituted phenyl group;

$Z^{102}$ is hydrogen, an optionally substituted alkyl group, an optionally substituted cycloalkyl group, an optionally substituted saturated or unsaturated heterocyclic group, or an optionally substituted saturated or unsaturated heterobicyclic group;

said substituted heterocyclic or substituted heterobicyclic group having one or more substituents each independently selected from the group consisting of hydroxyl, cyano, optionally substituted alkoxy, optionally substituted sulfonamido, optionally substituted ureido, optionally substituted carboxamido; optionally substituted amino, oxo, a saturated or unsaturated or aromatic optionally substituted heterocyclic group;

wherein the heterocyclic group comprises one or more nitrogen atoms, one or more oxygen atoms or a combination thereof and where said nitrogen atoms are independently optionally substituted by a substituted or unsubstituted alkyl, substituted or unsubstituted aryl, or substituted or unsubstituted arylalkyl; or $R^2$ is of the formula B-E;

B is hydroxy or an optionally substituted group selected from the group consisting of cycloalkyl, azacycloalkyl, amino, aminoalkylsulfonyl, alkoxyalkyl, alkoxy, aminoalklylcarbonyl, alkylenyl, aminoalkyl, alkylenylcarbonyl and aminoalkylcarbonyl;

E is an optionally substituted group selected from the group consisting of azacycloalkyl, azacycloalkylcarbonyl, azacycloalkylsulfonyl, azacycloalkylalkyl, heteroaryl, heteroarylcarbonyl, heteroarylsulfonyl, heteroarylalkyl, azacycloalkylcarbonylamino, heteroarylcarbonylamino and aryl; and n for each occurrence is independently an integer from 0 to 6.

A preferred compound of the foregoing compound of formula (I), denoted preferred group A, is where X is $CR^1$, Y is $CR_q$, Q is O and there is a double bond between X and Y; or X is $CR^1$, Y is N, Q is O and there is a double bond between X and Y; or X is $CR^1$, Y is O, Q is N and there is a double bond between Q and the pyrimidinyl ring.

A preferred compound of preferred group A, denoted preferred group B, is where the compound is of the formula (II),

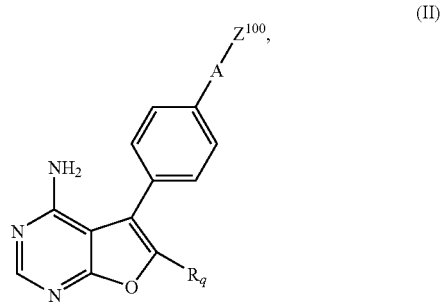

(II)

wherein $R_q$ is selected from the group consisting of hydrogen, alkoxyalkyl, alkyl, optionally substituted arylalkyl, optionally substituted cycloalkyl, optionally substituted cycloalkylalkyl, optionally substituted heteroaralkyl, optionally substituted (heterocycloalkyl)alkyl, and halo, wherein the arylalkyl, the cycloalkyl, the cycloalkylalkyl, the heteroaralkyl, and the (heterocycloalkyl)alkyl are each optionally substituted with one, two, three, four, or five substituents independently selected from the group consisting of alkoxy, alkoxyalkyl, alkyl, cyano, halo, haloalkyl, hydroxy, hydroxyalkyl, and nitro;

A is selected from the group consisting of —N(R)—C(O)—(CH$_2$)$_n$—N(R)—, —N(R)—, —N(R)C(O)—, and —N(R)S(O)$_p$—;

$Z^{100}$ is selected from the group consisting of optionally substituted aryl and optionally substituted heteroaryl;

n is 0; p is 2; and R is hydrogen.

A preferred compound of preferred group B, denoted preferred group C, is where R$_q$ is hydrogen.

A preferred compound of preferred group C, denoted preferred group D, is where the compound is:
N-[4-(4-aminofuro[2,3-d]pyrimidin-5-yl)phenyl]-N'-(4-methylphenyl)urea;
N-[4-(4-aminofuro[2,3-d]pyrimidin-5-yl)phenyl]-N'-(3-methylphenyl)urea;
N-[4-(4-aminofuro[2,3-d]pyrimidin-5-yl)phenyl]-N'-(2-methylphenyl)urea;
N-[4-(4-aminofuro[2,3-d]pyrimidin-5-yl)phenyl]-N'-(3-chlorophenyl)urea;
5-[4-(1,3-benzoxazol-2-ylamino)phenyl]furo[2,3-d]pyrimidin-4-amine;
N-[4-(4-aminofuro[2,3-d]pyrimidin-5-yl)phenyl]benzamide; or
N-[4-(4-aminofuro[2,3-d]pyrimidin-5-yl)phenyl]benzenesulfonamide.

Another preferred compound of preferred group B, denoted preferred group E, is where R$_q$ is selected from the group consisting of alkyl and halo.

A preferred compound of preferred group E, denoted preferred group F, is where the compound is:
N-[4-(4-amino-6-methylfuro[2,3-d]pyrimidin-5-yl)phenyl]-N'-(2-methylphenyl)urea;
N-[4-(4-amino-6-methylfuro[2,3-d]pyrimidin-5-yl)phenyl]-N'-(4-methylphenyl)urea;
N-[4-(4-amino-6-methylfuro[2,3-d]pyrimidin-5-yl)phenyl]benzamide;
N-[4-(4-amino-6-methylfuro[2,3-d]pyrimidin-5-yl)phenyl]benzenesulfonamide;
N-[4-(4-amino-6-methylfuro[2,3-d]pyrimidin-5-yl)phenyl]-N'-(3-methylphenyl)urea;
N-[4-(4-amino-6-methylfuro[2,3-d]pyrimidin-5-yl)phenyl]-N'-(3-chlorophenyl)urea;
N-[4-(4-amino-6-methylfuro[2,3-d]pyrimidin-5-yl)phenyl]-N'-(3-methoxyphenyl)urea;
N-[4-(4-amino-6-bromofuro[2,3-d]pyrimidin-5-yl)phenyl]-N'-(3-methylphenyl)urea;
N-[4-(4-amino-6-methylfuro[2,3-d]pyrimidin-5-yl)phenyl]-N'-(3-bromophenyl)urea;
N-[4-(4-amino-6-methylfuro[2,3-d]pyrimidin-5-yl)phenyl]-N'-(3-ethylphenyl)urea;
N-[4-(4-amino-6-methylfuro[2,3-d]pyrimidin-5-yl)phenyl]-N'-(3,5-dimethylphenyl)urea;
N-[4-(4-amino-6-methylfuro[2,3-d]pyrimidin-5-yl)phenyl]-N'-(3,5-dichlorophenyl)urea;
N-[4-(4-amino-6-methylfuro[2,3-d]pyrimidin-5-yl)phenyl]-N'-[2-fluoro-5-(trifluoromethyl)phenyl]urea;
1-[4-(4-Amino-6-methyl-furo[2,3-d]pyrimidin-5-yl)-phenyl]-3-(4-cyano-phenyl)-urea; or
1-[4-(4-Amino-6-methyl-furo[2,3-d]pyrimidin-5-yl)-phenyl]-3-(3-trifluoromethyl-phenyl)-urea.

Another preferred compound of preferred group A, denoted preferred group G, is where the compound is of formula (III),

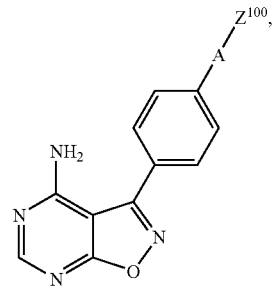

wherein

A is selected from the group consisting of a bond, —N(R)C(O)—, and —N(R)—C(O)—(CH$_2$)$_n$—N(R)—;

$Z^{100}$ is selected from the group consisting of —NO$_2$, amino, substituted amino, and optionally substituted aryl;

R is hydrogen; and n is 0.

A preferred compound of preferred group G, denoted preferred group H, is where A is a bond; and $Z^{100}$ is selected from the group consisting of —NO$_2$, substituted amino, and amino.

A preferred compound of preferred group H, denoted preferred group I, is:
3-(4-nitrophenyl)isoxazolo[5,4-d]pyrimidin-4-amine; or
3-(4-aminophenyl)isoxazolo[5,4-d]pyrimidin-4-amine.

Another preferred compound of preferred group G, denoted preferred group J, is where A is selected from the group consisting of —N(R)C(O)—, and —N(R)—C(O)—(CH$_2$), —N(R)—; and $Z^{100}$ is optionally substituted aryl.

A preferred compound of preferred group J, denoted preferred group K, is:
N-[4-(4-aminoisoxazolo[5,4-d]pyrimidin-3-yl)phenyl]-N'-(3-methylphenyl)urea;
N-[4-(4-aminoisoxazolo[5,4-d]pyrimidin-3-yl)phenyl]-N'-(3-ethylphenyl)urea;
N-[4-(4-aminoisoxazolo[5,4-d]pyrimidin-3-yl)phenyl]-N'-(3-chlorophenyl)urea;
N-[4-(4-aminoisoxazolo[5,4-d]pyrimidin-3-yl)phenyl]benzamide;
N-[4-(4-aminoisoxazolo[5,4-d]pyrimidin-3-yl)phenyl]-N'-[3-(trifluoromethyl)phenyl]urea; or
N-[4-(4-aminoisoxazolo[5,4-d]pyrimidin-3-yl)phenyl]-N'-[2-fluoro-5-(trifluoromethyl)phenyl]urea.

Another preferred compound of formula (I), denoted preferred group L, is where X is NR$^1$; both R$^3$ are each H; Y is N; Q is CR$^2$; and there is a double bond between Y and Q.

A preferred compound of preferred group L, denoted preferred group M, is
N2-{4-[7-Amino-3-(4-piperidyl)-1H-pyrazolo[4,3-d]pyrimidin-1-yl]-2-methoxyphenyl}-1-methyl-1H-2-indolecarboxamide;
N2-{4-[7-Amino-3-(4-piperidyl)-1H-pyrazolo[4,3-d]pyrimidin-1-yl]-2-methoxyphenyl}-2-fluoro-4-(trifluoromethyl)benzamide;
N1-[4-(7-Amino-1H-pyrazolo[4,3-d]pyrimidin-1-yl)-2-Methoxyphenyl]-2-fluoro-4-(trifluoromethyl)benzamide;
N1-{4-[7-Amino-3-(4-piperidyl)-1H-pyrazolo[4,3-d]pyrimidin-1-yl]-2-methoxyphenyl}-1-benzenesulfonamide;
Benzyl N-{4-[7-amino-3-(4-piperidyl)-1H-pyrazolo[4,3-d]pyrimidin-1-yl]-2-methoxyphenyl}carbamate;
N-{4-[7-Amino-3-(4-piperidyl)-1H-pyrazolo[4,3-d]pyrimidin-1-yl]-2-methoxyphenyl}-N-phenylurea;

N2-{4-[7-Amino-3-(1-tetrahydro-2H-4-pyranyl-4-piperidyl)-1H-pyrazolo[4,3-d]pyridin-1-yl]-2-methoxyphenyl}-1-methyl-1H-2-indolecarboxamide;

N2-{4-[7-amino-3-(1-ethyl-4-piperidyl)-1H-pyrazolo[4,3-d]pyrimidin-1-yl]-2-methoxyphenyl}-1-methyl-1H-2-indolecarboxamide;

N1-{4-[7-Amino-3-(4-piperidyl)-1H-pyrazolo[4,3-d]pyrimidin-1-yl]phenyl}-1-benzenesulfonamide;

N2-{4-[7-Amino-3-(4-piperidyl)-1H-pyrazolo[4,3-d]pyrimidin-1-yl]phenyl}-1-methyl-1H-2-indolecarboxamide; or N2-{4-[7-Amino-3-(1,2,3,6-tetrahydro-4-pyridinyl)-1H-pyrazolo[4,3-d]pyrimidin-1-yl]-2-methoxyphenyl}-1-methyl-1H-2-indolecarboxamide.

Another preferred compound of formula (I), denoted preferred group N, is where X is $CR^1$; one of $R^3$ is not H; Y is N, Q is $NR^2$; and there is a double bond between X and Y.

In another aspect the present invention is directed to the use of any compound encompassed by formula (I), including the species enumerated herein, for any of the methods described herein, such as:

a method of inhibiting one or more protein kinase activity in a patient comprising administering a therapeutically effective amount of a compound of formula (I) or a physiologically acceptable salt, prodrug or biologically active metabolites thereof to said patient;

a method wherein said protein kinase is selected from the group consisting of KDR, FGFR-1, PDGFRβ, PDGFRα, IGF-1R, c-Met, Flt-1, Flt-4, TIE-2, TIE-1, Lck, Src, fyn, Lyn, Blk, hck, fgr and yes;

a method of affecting hyperproliferative disorders in a patient comprising administering a therapeutically effective amount of a compound of formula (I) or a physiologically acceptable salt, prodrug or biologically active metabolites thereof to said patient;

a method of affecting angiogenesis in a patient comprising administering a therapeutically effective amount of a compound of formula (I) or a physiologically acceptable salt, prodrug or biologically active metabolites thereof to said patient;

a method wherein the protein kinase is a protein serine/threonine kinase or a protein tyrosine kinase;

a method of treating one or more ulcers in a patient comprising administering a therapeutically effective amount of a compound of formula (I) or a physiologically acceptable salt, prodrug or biologically active metabolites thereof to said patient;

a method wherein the ulcer or ulcers are caused by a bacterial or fungal infection; or the ulcer or ulcers are Mooren ulcers; or the ulcer or ulcers are a symptom of ulcerative colitis;

a method of treating a condition in a patient comprising administering a therapeutically effective amount of a compound of formula (I) or a physiologically acceptable salt, prodrug or biologically active metabolites thereof to said patient, wherein said condition is an ocular condition, a cardiovascular condition, a cancer, Crow-Fukase (POEMS) syndrome, a diabetic condition, sickle cell anaemia, chronic inflammation, systemic lupus, glomerulonephritis, synovitis, inflammatory bowel disease, Crohn's disease, glomerulonephritis, rheumatoid arthritis, osteoarthritis, multiple sclerosis, graft rejection, Lyme disease, sepsis, von Hippel Lindau disease, pemphigoid, psoriasis, Paget's disease, polycystic kidney disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis;

a method wherein the ocular condition is ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy or macular degeneration;

a method wherein the cardiovascular condition is atherosclerosis, restenosis, ischemia/reperfusion injury, vascular occlusion or carotid obstructive disease;

a method wherein the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, Kaposi's sarcoma, Hodgkin's disease, lymphoma, myeloma, leukemia or malignant ascites;

a method wherein the diabetic condition is insulin-dependent diabetes mellitus glaucoma, diabetic retinopathy or microangiopathy;

a method of decreasing fertility in a patient, said method comprising the step of administering to the patient an effective amount of a compound of formula (I) or a physiologically acceptable salt, prodrug or biologically active metabolite thereof;

a method wherein the compound or a physiologically acceptable salt, prodrug or biologically active metabolite thereof is administered in an amount effective to promote angiogenesis or vasculogenesis;

a method wherein the protein kinase is TIE-2;

a method wherein the compound of formula (I), or physiologically acceptable salt, prodrug or biologically active metabolite thereof, is administered in combination with a pro-angiogenic growth factor;

a method wherein the pro-angiogenic growth factor is selected from the group consisiting of VEGF, VEGF-B, VEGF-C, VEGF-D, VEGF-E, HGF, FGF-1, FGF-2, derivatives thereof and antiiodotypic antibodies;

a method wherein the patient is suffering from anemia, ischemia, infarct, transplant rejection, a wound, gangrene or necrosis; or a method wherein the protein kinase activity is involved in T cell activation, B cell activation, mast cell degranulation, monocyte activation, the potentiation of an inflammatory response or a combination thereof.

In another aspect, the present invention is directed to a pharmaceutical composition comprising a compound of formula (I) and a pharmaceutically acceptable carrier or diluent.

DETAILED DESCRIPTION OF THE INVENTION

Progression through the eukaryotic cell cycle is controlled by a family of kinases called cyclin dependent kinases (CDKs) (Myerson et al., *EMBO Journal*, 11:2909-2917 (1992)). The regulation of CDK activation is complex, but requires the association of the CDK with a member of the cyclin family of regulatory subunits (Draetta, *Trends in Cell Biology*, 3:287-289 (1993)); Murray and Kirschner, *Nature*, 339:275-280 (1989); Solomon et al., *Molecular Biology of the Cell*, 3:13-27 (1992)). A further level of regulation occurs through both activating and inactivating phosphorylations of the CDK subunit (Draetta, *Trends in Cell Biology*, 3:287-289 (1993)); Murray and Kirschner, *Nature*, 339:275-280 (1989); Solomon et al., *Molecular Biology of the Cell*, 3:13-27

(1992); Ducommun et al., *EMBO Journal*, 10:3311-3319 (1991); Gautier et al., *Nature* 339:626-629 (1989); Gould and Nurse, *Nature*, 342:39-45 (1989); Krek and Nigg, *EMBO Journal*, 10:3331-3341 (1991); Solomon et al., *Cell*, 63:1013-1024 (1990)). The coordinate activation and inactivation of different cyclin/CDK complexes is necessary for normal progression through the cell cycle (Pines, *Trends in Biochemical Sciences*, 18:195-197 (1993); Sherr, *Cell*, 73:1059-1065 (1993)). Both the critical G1-S and G 2-M transitions are controlled by the activation of different cyclin/CDK activities. In G1, both cyclin D/CDK4 and cyclin E/CDK2 are thought to mediate the onset of S-phase (Matsushima et al., *Molecular & Cellular Biology*, 14:2066-2076 (1994); Ohtsubo and Roberts, *Science*, 259:1908-1912 (1993); Quelle et al., *Genes & Development*, 7:1559-1571 (1993); Resnitzky et al., *Molecular & Cellular Biology*, 14:1669-1679 (1994)). Progression through S-phase requires the activity of cyclin A/CDK2 (Girard et al., *Cell*, 67:1169-1179 (1991); Pagano et al., *EMBO Journal*, 11:961-971 (1992); Rosenblatt et al., *Proceedings of the National Academy of Science USA*, 89:2824-2828 (1992); Walker and Maller, *Nature*, 354:314-317 (1991); Zindy et al., *Biochemical & Biophysical Research Communications*, 182:1144-1154 (1992)) whereas the activation of cyclin A/cdc2 (CDK1) and cyclin B/cdc2 are required for the onset of metaphase (Draetta, *Trends in Cell Biology*, 3:287-289 (1993)); Murray and Kirschner, *Nature*, 339:275-280 (1989); Solomon et al., *Molecular Biology of the Cell*, 3:13-27 (1992); Girard et al., *Cell*, 67:1169-1179 (1991); Pagano et al., *EMBO Journal*, 11:961-971 (1992); Rosenblatt et al., *Proceedings of the National Academy of Science USA*, 89:2824-2828 (1992); Walker and Maller, *Nature*, 354:314-317 (1991); Zindy et al., *Biochemical & Biophysical Research Communications*, 182: 1144-1154 (1992)). It is not surprising, therefore, that the loss of control of CDK regulation is a frequent event in hyperproliferative diseases and cancer. (Pines, *Current Opinion in Cell Biology*, 4:144-148 (1992); Lees, *Current Opinion in Cell Biology*, 7:773-780 (1995); Hunter and Pines, *Cell*, 79:573-582 (1994)). The selective inhibition of CDKs is therefore an object of the present invention.

The compounds of the present invention are additionally useful in the treatment of one or more diseases afflicting mammals which are characterized by cellular proliferation in the areas of blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, diabetic nephropathy, malignant nephrosclerosis, thrombotic microangiopathy syndromes, organ transplant rejection and glomerulopathies. Metabolic disorders include psoriasis, diabetes mellitus, chronic wound healing, inflammation, neurodegenerative diseases, macular degeneration, and diabetic retinopathy.

Inhibitors of kinases involved in mediating or maintaining these disease states represent novel therapies for these disorders. Examples of such kinases include, but are not limited to: (1) inhibition of c-Src (Brickell, *Critical Reviews in Oncogenesis*, 3:401-406 (1992); Courtneidge, *Seminars in Cancer Biology*, 5:236-246 (1994), raf (Powis, *Pharmacology & Therapeutics*, 62:57-95 (1994)) and the cyclin-dependent kinases (CDKs) 1, 2 and 4 in cancer (Pines, *Current Opinion in Cell Biology*, 4:144-148 (1992); Lees, *Current Opinion in Cell Biology*, 7:773-780 (1995); Hunter and Pines, *Cell*, 79:573-582 (1994)), (2) inhibition of CDK2 or PDGF-R kinase in restenosis (Buchdunger et al., *Proceedings of the National Academy of Science USA*, 92:2258-2262 (1995)), (3) inhibition of CDK5 and GSK3 kinases in Alzheimers (Hosoi et al., *Journal of Biochemistry* (Tokyo), 117:741-749 (1995); Aplin et al., *Journal of Neurochemistry*, 67:699-707 (1996), (4) inhibition of c-Src kinase in osteoporosis (Tanaka et al., *Nature*, 383:528-531 (1996), (5) inhibition of GSK-3 kinase in type-2 diabetes (Borthwick et al., *Biochemical & Biophysical Research Communications*, 210:738-745 (1995), (6) inhibition of the p38 kinase in inflammation (Badger et al., *The Journal of Pharmacology and Experimental Therapeutics*, 279:1453-1461 (1996)), (7) inhibition of VEGF-R1-3 and TIE-1 and -2 kinases in diseases which involve angiogenesis (Shawver et al., *Drug Discovery Today*, 2:50-63 (1997)), (8) inhibition of UL97 kinase in viral infections (He et al., *Journal of Virology*, 71:405-411 (1997)), (9) inhibition of CSF-1R kinase in bone and hematopoetic diseases (Myers et al., *Bioorganic & Medicinal Chemistry Letters*, 7:421-424 (1997), and (10) inhibition of Lck kinase in autoimmune diseases and transplant rejection (Myers et al., *Bioorganic & Medicinal Chemistry Letters*, 7:417-420 (1997)).

It is additionally possible that inhibitors of certain kinases may have utility in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al., *Cancer Research*, 56:3199-3202 (1996); Kohn et al., *Journal of Cellular Biochemistry*, 54:44-452 (1994)). Inhibition of CDKs 2 or 4 will prevent progression into the cycle in normal cells and limit the toxicity of cytotoxics which act in S-phase, G2 or mitosis. Furthermore, CDK2/cyclin E activity has also been shown to regulate NF-kB. Inhibition of CDK2 activity stimulates NF-kB-dependent gene expression, an event mediated through interactions with the p300 coactivator (Perkins et al., *Science*, 275:523-527 (1997)). NF-kB regulates genes involved in inflammatory responses (such as hematopoetic growth factors, chemokines and leukocyte adhesion molecules) (Baeuerle and Henkel, *Annual Review of Immunology*, 12:141-179 (1994)) and may be involved in the suppression of apoptotic signals within the cell (Beg and Baltimore, *Science*, 274:782-784 (1996); Wang et al., *Science*, 274:784-787 (1996); Van Antwerp et al., *Science*, 274:787-789 (1996)). Thus, inhibition of CDK2 may suppress apoptosis induced by cytotoxic drugs via a mechanism which involves NF-kB. This therefore suggests that inhibition of CDK2 activity may also have utility in other cases where regulation of NF-kB plays a role in etiology of disease. A further example may be take from fungal infections: Aspergillosis is a common infection in immune-compromised patients (Armstrong, *Clinical Infectious Diseases*, 16:1-7 (1993)). Inhibition of the *Aspergillus* kinases Cdc2/CDC28 or Nim A (Osmani et al., *EMBO Journal*, 10:2669-2679 (1991); Osmani et al., *Cell*, 67:283-291 (1991)) may cause arrest or death in the fungi, improving the therapeutic outcome for patients with these infections.

The following are the preferred substituents of a compound of formula (I). Preferably, $R_a$ and $R_b$ are each independently F, Cl, Br, I, $CH_3$, $NO_2$, $OCF_3$, $OCH_3$, CN, $CO_2CH_3$, $CF_3$, t-butyl, pyridyl, carboxyl, or an optionally substituted group selected from the group consisting of oxazolyl, benzyl, benzenesulfonyl, phenoxy, phenyl, amino, tetrazolyl, styryl, arylthio and heteroarylthio; CH₂OR$_c$, wherein R$_e$ is hydrogen or optionally substituted alkyl or aryl; and —W—(CH₂)$_t$—NR$_d$R$_e$, wherein t is an integer from about 1 to about 6; W is a direct bond, O, S, S(O), S(O)₂, or NR$_f$, wherein R$_f$ is H or alkyl and R$_d$ and R$_e$ are independently H, alkyl, alkanoyl or SO₂-alkyl; or R$_d$, R$_e$ and the nitrogen atom to which they are attached together form a five- or six-membered heterocyclic ring.

In one embodiment, R² is an oxacycloalkyl group of the formula

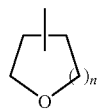

wherein n is 1, 2 or 3.

In another embodiment, R₂ is of the formula

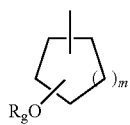

where m is 0, 1, 2 or 3 and R$_g$ is H or —(CH₂)$_p$N(R₄)R₅, where p is an integer from about 2 to about 6. R₄ and R₅ are each, independently, H, azabicycloalkyl or Y—Z, wherein Y is selected from the group consisting of —C(O)—, —(CH₂)$_p$—, —S(O)₂—, —C(O)O—, —SO₂NH—, —CONH—, (CH₂)$_q$O—, —(CH₂)$_q$NH—, and —(CH₂)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group or R₄, R₅ and the nitrogen atom together form a 3, 4, 5, 6 or 7-membered, substituted or unsubstituted heterocyclic or heterobicyclic group.

In another embodiment, R₂ is of the formula

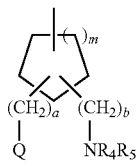

wherein m is 1, 2 or 3. a and b are each, independently, an integer from 0 to about, except that when the two substituents are attached to the same carbon atom, a is from 1 to about 6. Q is NR₄R₅ or —OR₆. Each R₄ and R₅ is, independently, H, azabicycloalkyl or Y—Z, wherein Y is selected from the group consisting of —C(O)—, —(CH₂)$_p$—, —S(O)₂—, —C(O)O—, —SO₂NH—, —CONH—, (CH₂)$_q$O—, —(CH₂)$_q$NH—, and —(CH₂)$_q$S(O)$_r$—; where p is an integer from 0 to about 6, q is an integer from 0 to about 6, and r is 0, 1 or 2; and Z is a substituted or unsubstituted alkyl, amino, aryl, heteroaryl or heterocycloalkyl group. R₄, R₅ and the nitrogen atom can also together form a 3, 4, 5, 6 or 7-membered, substituted or unsubstituted heterocyclic or heterobicyclic group.

In another embodiment, R₂ is of the formula

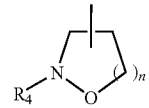

where n is 1, 2 or 3; and R₄ is H, azabicycloalkyl or Y—Z, wherein Y is selected from the group consisting of —C(O)—, —(CH₂)$_p$—, —S(O)₂—, —C(O)O—, —SO₂NH—, —CONR—, (CH₂)$_q$O, —(CH₂)$_q$NH—, and —(CH₂)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group.

In another embodiment, R₂ is of the formula

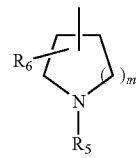

where m is 0, 1, 2 or 3. R₅ is H, azabicycloalkyl or Y—Z, where Y is selected from the group consisting of —C(O)—, —(CH₂)$_p$—, —S(O)₂—, —C(O)O—, —SO₂NH—, —CONH—, —(CH₂)$_q$O—, —(CH₂)$_q$NH—, and —(CH₂)$_q$S(O)$_r$—; where p is an integer from 0 to about 6, q is an integer from 0 to about 6, and r is 0, 1 or 2; and Z is a substituted or unsubstituted alkyl, amino, aryl, heteroaryl or heterocycloalkyl group. R₆ represents one or more substituents independently selected from the group consisting of hydrogen, hydroxy, oxo and substituted or unsubstituted alkyl, aryl, heteroaryl, alkoxycarbonyl, alkoxyalkyl, aminocarbonyl, alkylcarbonyl, arylcarbonyl, heteroarylcarbonyl, aminoalkyl and arylalkyl groups, provided that the carbon atoms adjacent to the nitrogen atom are not substituted by a hydroxy group.

In another embodiment, R₂ is of the formula

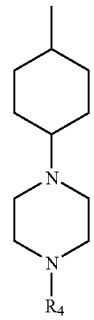

wherein R₄ is H, azabicycloalkyl or Y—Z, wherein Y is selected from the group consisting of —C(O)—, —(CH₂)$_p$—, —S(O)₂—, —C(O)O—, —SO₂NH—, —CONH—, (CH₂)$_q$O—, —(CH₂)$_q$NH—, and —(CH₂)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group.

In another embodiment, $R_2$ is of the formula

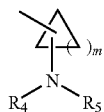

where m is an integer from 1 to about 6; and $R_4$ and $R_5$ are each, independently, H, azabicycloalkyl or Y—Z, wherein Y is selected from the group consisting of —C(O)—, $(CH_2)_p$—, —S(O)$_2$—, —C(O)O—, —SO$_2$NH—, —CONH—, $(CH_2)_q$O—, $(CH_2)_q$NH—, and —$(CH_2)_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_4$, $R_5$ and the nitrogen atom can also together form a 3, 4, 5, 6 or 7-membered, substituted or unsubstituted heterocyclic or heterobicyclic group.

In another embodiment, $R_2$ is of the formula

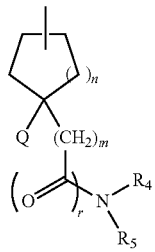

where n is an integer from 0 to about 4; and r is 0 or 1. When r is 0, m is an integer from 0 to 6. When r is 1, m is an integer from 1 to 6. Q is —NR$_4$R$_5$ or —OR$_6$. Each $R_4$ and $R_5$ is, independently, H, azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, (CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_4$, $R_5$ and the nitrogen atom can also together form a 3, 4, 5 or 6-membered, substituted or unsubstituted heterocyclic group. $R_6$ is hydrogen or a substituted or unsubstituted alkyl group.

In another embodiment, $R_2$ is of the formula

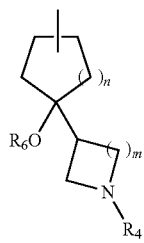

where n is an integer from 0 to about 4 and m is an integer from 0 to about 6. $R_4$ is H, azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, (CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_6$ is hydrogen or a substituted or unsubstituted alkyl group.

In embodiments of $R_2$ described above which include an —N(R$_4$)R$_5$ group, this group can form a heterocyclic group of the formula

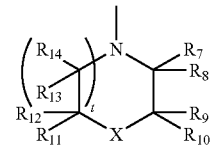

where $R_7$, $R_8$, $R_9$, $R_{10}$, $R_{11}$, $R_{12}$, $R_{13}$ and $R_{14}$ are each, independently, lower alkyl or hydrogen; or at least one pair of substituents $R_7$ and $R_8$; $R_9$ and $R_{10}$; $R_{11}$, and $R_{12}$; or $R_{13}$ and $R_{14}$ together are an oxygen atom; or at least one of $R_7$ and $R_9$ is cyano, CONHR$_{15}$, COOR$_{15}$, CH$_2$OR$_{15}$ or CH$_2$NR$_{15}$(R$_{16}$), where $R_{15}$ and $R_{16}$ are each, independently, H, azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group; or $R_{15}$, $R_{16}$ and the nitrogen atom together form a 3, 4, 5, 6 or 7-membered, substituted or unsubstituted heterocyclic or heterobicyclic group; X is O, S, SO, SO$_2$, CH$_2$, CHOR$_{17}$ or NR$_{17}$, wherein $R_{17}$ is hydrogen, substituted or unsubstituted alkyl, aryl, arylalkyl, —C(NH)NH$_2$, —C(O)R$_{17}$, or —C(O)OR$_{18}$, wherein $R_{18}$ is hydrogen, substituted or unsubstituted alkyl, aryl or arylalkyl; and t is 0 or 1.

$R_4$, $R_5$ and the nitrogen atom can also together form a heterocyclic group of the formula

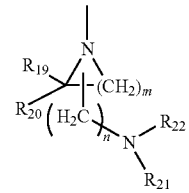

where $R_{19}$ and $R_{20}$ are each, independently, hydrogen or lower alkyl; or $R_{19}$ and $R_{20}$ together are an oxygen atom. $R_{21}$ and $R_{22}$ are each, independently, H azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_{21}$, $R_{22}$ and the nitrogen atom can also together form a 3, 4, 5 or 6-membered, substituted or unsubstituted heterocyclic group. m is an integer from 1 to about 6; and n is an integer from 0 to about 6.

$R_4$, $R_5$ and the nitrogen atom can also together form a heterocyclic group of the formula

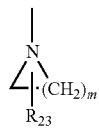

where m is an integer from 1 to 6. $R_{23}$ is $CH_2OH$, NRR', C(O)NR'R or COOR, where R and R' are each independently hydrogen or a substituted or unsubstituted alkyl, aryl or arylalkyl group.

$R_4$, $R_5$ and the nitrogen atom can also together form a heterocyclic group of the formula

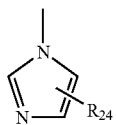

where $R_{24}$ is a substituted or unsubstituted alkyl, aryl or arylalkyl group, carboxyl, cyano, $C(O)OR_{25}$, $CH_2OR_{25}$, $CH_2NR_{26}R_{27}$ or $C(O)NHR_{26}$. $R_{25}$ is a substituted or unsubstituted alkyl, aryl, arylalkyl, heterocyclic or heteroaryl group. $R_{26}$ and $R_{27}$ are each, independently, H, azabicycloalkyl or Y—Z, wherein Y is selected from the group consisting of —C(O)—, —$(CH_2)_p$—, —$S(O)_2$—, —C(O)O—, —$SO_2NH$—, —CONH—, $(CH_2)_qO$—, —$(CH_2)_qNH$—, and —$(CH_2)_qS(O)_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. $R_{26}$, $R_{27}$ and the nitrogen atom can also together form a 3, 4, 5 or 6-membered, substituted or unsubstituted heterocyclic group.

In one subset of compounds of formula (I), at least one of $R_4$ and $R_5$ is of the formula Y—Z, where Z is of the formula

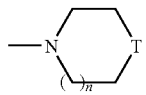

where T is C(O), S, SO, $SO_2$, CHOR or NR, wherein R is hydrogen or a substituted or unsubstituted alkyl, aryl or arylalkyl group; and n is 0, 1 or 2.

In another embodiment, at least one of $R_4$ and $R_5$ is of the formula Y—Z, where Z is —$N(R_{28})R_{29}$, and $R_{28}$ and $R_{29}$ are each, independently, substituted or unsubstituted carboxyalkyl, alkoxycarbonylalkyl, hydroxyalkyl, alkylsulfonyl, alkylcarbonyl or cyanoalkyl. $R_{28}$ and $R_{29}$, together with the nitrogen atom, can also form a five- or six-membered heterocyclic group.

In yet another embodiment, at least one of $R_4$ and $R_5$ is of the formula Y—Z, where Z is of the formula $N(R_{30})R_{31}$. $R_{30}$ and $R_{31}$ are each, independently, hydrogen, alkyl, alkoxycarbonyl, alkoxyalkyl, hydroxyalkyl, aminocarbonyl, cyano, alkylcarbonyl or arylalkyl.

In another embodiment, at least one of $R_4$ and $R_5$ is Y—Z, where Z is of the formula

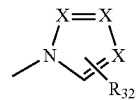

Each X is, independently, CH or N. $R_{32}$ is hydrogen, cyano or a substituted or unsubstituted alkyl, alkoxycarbonyl, alkoxyalkyl, hydroxyalkyl, aminocarbonyl, alkylcarbonyl or arylalkyl group.

One of $R_4$ and $R_5$ can also be Y—Z where Z is of the formula

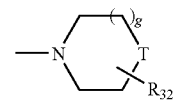

where g is 0 or 1; and T is C(O), O, S, SO, $SO_2$, $CH_2$, $CHOR_{17}$ or $NR_{17}$. $R_{17}$ is hydrogen, substituted or unsubstituted alkyl, aryl, arylalkyl, —$C(NH)NH_2$, —$C(O)R_{18}$, $C(O)NH_2$ or —$C(O)OR_{18}$, where $R_{18}$ is hydrogen, substituted or unsubstituted alkyl, aryl or arylalkyl. $R_{32}$ is hydrogen, cyano or a substituted or unsubstituted alkyl, alkoxycarbonyl, alkoxyalkyl, hydroxyalkyl, aminocarbonyl, alkylcarbonyl or arylalkyl group.

One of $R_4$ and $R_5$ can also be Y—Z, where Z is of the formula

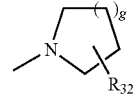

where g is 0, 1 or 2; and $R_{32}$ is hydrogen, cyano or a substituted or unsubstituted alkyl, alkoxycarbonyl, alkoxyalkyl, hydroxyalkyl, aminocarbonyl, alkylcarbonyl or arylalkyl group.

Z can also be of the formula

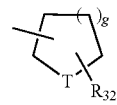

where g is 0, 1, 2 or 3, and T is O, S, SO, $SO_2$, $CH_2$, $CHOR_{17}$ or $NR_{17}$. $R_{17}$ is hydrogen, substituted or unsubstituted alkyl, aryl, arylalkyl, —$C(NH)NH_2$, —$C(O)R_{17}$, or —$C(O)OR_{18}$, wherein $R_{18}$ is hydrogen, substituted or unsubstituted alkyl, aryl or arylalkyl. $R_{32}$ is hydrogen, cyano or a substituted or unsubstituted alkyl, alkoxycarbonyl, alkoxyalkyl, hydroxyalkyl, aminocarbonyl, alkylcarbonyl or arylalkyl group.

One of $R_4$ and $R_5$ can also be Y—Z, wherein Z is of the formula

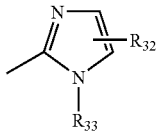

Where $R_{32}$ is hydrogen, cyano or substituted or unsubstituted alkyl, alkoxycarbonyl, alkoxyalkyl, hydroxyalkyl, aminocarbonyl, alkylcarbonyl, thioalkoxy or arylalkyl; and $R_{33}$ is hydrogen or substituted or unsubstituted alkyl, alkoxycarbonyl, alkoxyalkyl, aminocarbonyl, perhaloalkyl, alkenyl, alkylcarbonyl or arylalkyl.

In another subset of the compounds of formula (I), $R_2$ is of the formula

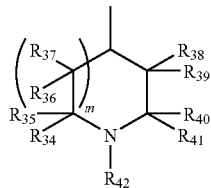

where m is 0 or 1; $R_{34}$, $R_{35}$, $R_{36}$, $R_{37}$, $R_{38}$, $R_{39}$, $R_{40}$ and $R_{41}$ are each, independently, methyl or hydrogen; or at least one pair of substituents $R_{34}$ and $R_{35}$; $R_{36}$ and $R_{37}$; $R_{38}$ and $R_{39}$; or $R_{40}$ and $R_{41}$ together are an oxygen atom. $R_{42}$ is H, azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group.

In a preferred embodiment, $R_{42}$ is of the formula

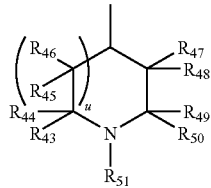

Where u is 0 or 1; $R_{43}$, $R_{44}$, $R_{45}$, $R_{46}$, $R_{47}$, $R_{48}$, $R_{49}$ and $R_{50}$ are each, independently, methyl or hydrogen; or at least one pair of substituents $R_{43}$ and $R_{44}$; $R_{45}$ and $R_{46}$; $R_{47}$ and $R_{48}$; or $R_{49}$ and $R_{50}$ together are an oxygen atom. $R_{51}$ is H, azabicycloalkyl or V-L, where V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and L is a substituted or unsubstituted alkyl, amino, aryl, heteroaryl or heterocycloalkyl group.

In another subset of the compounds of formula (I), $R_2$ is of the formula

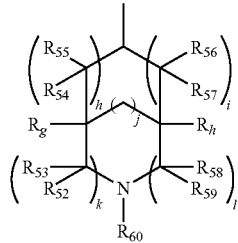

Where h, i, j, k and l are independently 0 or 1; $R_{52}$, $R_{53}$, $R_{54}$, $R_{55}$, $R_{56}$, $R_{57}$, $R_{58}$, $R_{59}$, $R_g$ and $R_h$ are each, independently, methyl or hydrogen; or at least one pair of substituents $R_{52}$ and $R_{53}$; $R_{54}$ and $R_{55}$; $R_{56}$ and $R_{57}$; or $R_{58}$ and $R_{59}$ together are an oxygen atom. $R_{60}$ is H, azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and Z is a substituted or unsubstituted alkyl, amino, aryl, heteroaryl or heterocycloalkyl group. In one embodiment, $R_{60}$ is of the formula

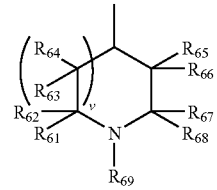

Where v is 0 or 1; $R_{61}$, $R_{62}$, $R_{63}$, $R_{64}$, $R_{65}$, $R_{66}$, $R_{67}$ and $R_{68}$ are each, independently, lower alkyl or hydrogen; or at least one pair of substituents $R_6$, and $R_{62}$; $R_{63}$ and R; $R_{65}$ and $R_{66}$; and $R_{67}$ and $R_{68}$ together are an oxygen atom; and $R_{69}$ is H, azabicycloalkyl or V-L, where V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to about 6, q is an integer from 0 to about 6, and r is 0, 1 or 2; and L is a substituted or unsubstituted alkyl, amino, aryl, heteroaryl or heterocycloalkyl group.

Compounds of formula (I) may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures), succinates, benzoates and salts with amino acids such as glutamic acid. These salts may be prepared by methods known to those skilled in the art.

Certain compounds of formula (I) which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formula (I) and their salts may exist in more than one crystal form and the present invention includes each crystal form and mixtures thereof.

Certain compounds of formula (I) and their salts may also exist in the form of solvates, for example hydrates, and the present invention includes each solvate and mixtures thereof.

Certain compounds of formula (I) may contain one or more chiral centres, and exist in different optically active forms. When compounds of formula (I) contain one chiral centre, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula (I) contains more than one chiral centre it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula (I) and mixtures thereof.

Certain compounds of formula (I) may exist in different tautomeric forms or as different geometric isomers, and the present invention includes each tautomer and/or geometric isomer of compounds of formula (I) and mixtures thereof.

Certain compounds of formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula (I) and mixtures thereof.

Certain compounds of formula (I) may exist in zwitterionic form and the present invention includes each zwitterionic form of compounds of formula (I) and mixtures thereof. Heteroaromatic groups, as used herein, include heteroaryl ring systems (e.g., for purposes of exemplification, which should not be construed as limiting the scope of this invention: thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isothiazoles, oxazolyl or tetrazoles) and heteroaryl ring systems in which a carbocyclic aromatic ring, carbocyclic non-aromatic ring or heteroaryl ring is fused to one or more other heteroaryl rings (e.g., for purposes of exemplification, which should not be construed as limiting the scope of this invention: benzo(b)thienyl, benzimidazolyl, benzoxazolyl, benzothiazolyl, benzothiadiazolyl, benzoxadiazolyl, indole, tetrahydroindole, azaindole, indazole, quinoline, imidazopyridine, quinazoline purine, pyrrolo[2,3-d]pyrimidine, pyrazolo[3,4-d]pyrimidine) and their N-oxides. Substituted heteroaryl groups are preferably substituted with one or more substituents each independently selected from the group consisting of a halogen, hydroxy, alkyl, alkoxy, alkyl-O—C(O)—, alkoxyalkyl, a heterocycloalkyl group, optionally substituted phenyl, nitro, amino, mono-substituted amino or di-substituted amino.

A heterocyclic (heterocyclyl) group, as used herein, refers to a heterocyclic group that is unsaturated, partially saturated or saturated.

A heterobicyclic group, as used herein, refers to a bicyclic group having one or more heteroatoms, which is saturated, partially unsaturated or unsaturated.

An arylalkyl group, as used herein, is an aromatic substituent that is linked to a compound by an aliphatic group having from one to about six carbon atoms. A preferred arylalkyl group is a benzyl group.

An heteroaralkyl group, as used herein, is a heteroaromatic substituent that is linked to a compound by an aliphatic group having from one to about six carbon atoms.

A heterocycloalkyl group, as used herein, is a non-aromatic ring system that has 3 to 8 atoms and includes at least one heteroatom, such as nitrogen, oxygen, or sulfur.

As used herein, a (heterocycloalkyl)alkyl group is a heterocycloalkyl group attached to the parent molecule through an alkyl group.

As used herein, a cycloalkyl group is a saturated or partially unsaturated monocyclic, bicyclic, or tricyclic hydrocarbon ring system having three to twelve carbon atoms.

As used herein, a cycloalkylalkyl group is a cycloalkyl group attached to the parent molecule through an alkyl group.

As used herein, aliphatic groups or notations such as "($C_0$-$C_6$)" include straight chained, branched or cyclic hydrocarbons which are completely saturated or which contain one or more units of unsaturation. When the group is a $C_0$ it means that the moiety is not present or in other words is a bond.

As used herein, an alkoxyalkyl group is an alkoxy group that is attached to the parent molecule through an alkyl group. Preferred are alkoxy groups of 1 to 6 carbon atoms and alkyl groups of 1 to 6 carbon atoms.

As used herein, aromatic groups (or aryl groups) include aromatic carbocyclic ring systems (e.g. phenyl) and fused polycyclic aromatic ring systems (e.g. naphthyl and 1,2,3,4-tetrahydronaphthyl).

As used herein, the term "natural amino acid" refers to the twenty-three natural amino acids known in the art, which are as follows (denoted by their three letter acronym): Ala, Arg, Asn, Asp, Cys, Cys-Cys, Glu, Gln, Gly, His, Hyl, Hyp, Ele, Leu, Lys, Met, Phe, Pro, Ser, Thr, Trp, Tyr, and Val. The term non-natural amino acid refers to compounds of the formula $NH_2$—$(C(X)_2)_n$—COOH, which are alpha—(when n is 1) or beta—(when n is 2) amino acids where X for each occurrence is independently any side chain moiety recognized by those skilled in the art; examples of non-natural amino acids include, but are not limited to: hydroxyproline, homoproline, 4-amino-phenylalanine, β-(2-naphthyl)alanine, norleucine, cyclohexylalanine, β-(3-pyridinyl)alanine, β-(4-pyridinyl)alanine, α-aminoisobutyric acid, urocanic acid, N,N-tetramethylamidino-histidine, N-methyl-alanine, N-methyl-glycine, N-methyl-glutamic acid, tert-butylglycine, α-aminobutyric acid, tert-butylalanine, ornithine, α-aminoisobutyric acid, β-alanine, γ-aminobutyric acid, 5-aminovaleric acid, 12-aminododecanoic acid, 2-aminoindane-2-carboxylic acid, etc. and the derivatives thereof, especially where the amine nitrogen has been mono- or di-alkylated.

As used herein, many moieties or substituents are termed as being either "substituted or unsubstituted" or "optionally substituted". When a moiety is modified by one of these terms, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkyl groups (which itself can also be substituted, such as $CF_3$), alkoxy group (which itself can be substituted, such as $OCF_3$), a halogen or halo group (F, Cl, Br, I), hydroxy, nitro, oxo, CN, COH, COOH, amino, N-alkylamino or N,N-dialkylamino (in which the alkyl groups can also be substituted), esters (—C(O)—OR, where R is groups such as alkyl, aryl, etc., which can be substituted), aryl (most preferred is phenyl, which can be substituted) and arylalkyl (which can be substituted).

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, restenosis, psoriasis, hemangiomas, myocardial angiogenesis, coronary and cerebral collaterals, ischemic limb angiogenesis, ischemia/reperfusion injury, wound healing, peptic ulcer *Helicobacter* related diseases, virally-induced angiogenic disorders, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Further, some of these compounds can be used as active agents against burns, chronic lung disease, stroke, polyps, anaphylaxis, chronic and allergic inflammation, delayed-type hypersensitivity, ovarian hyperstimulation syndrome, brain tumor-associated cerebral edema, high-altitude, trauma or hypoxia induced cerebral or pulmonary edema, ocular and macular edema, ascites, glomerulonephritis and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome). Increased VEGF production potentiates inflammatory processes such as monocyte recruitment and activation. The compounds of this invention will also be useful in treating inflammatory disorders such as inflammatory bowel disease (IBD) and Crohn's disease.

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

Because blastocyst implantation, placental development and embryogenesis are angiogenesis dependent, certain compounds of the invention are useful as contraceptive agents and antifertility agents.

It is envisaged that the disorders listed above are mediated to a significant extent by protein tyrosine kinase activity involving the KDR/VEGFR-2 and/or the Flt-1/VEGFR-1 and/or TIE-2 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used. Certain compounds of the invention are also effective inhibitors of FGFR, PDGFR, c-Met and IGF-1-R. These receptor kinases can directly or indirectly potentiate angiogenic and hyperproliferative responses in various disorders, hence their inhibition can impede disease progression.

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovasculatization. By adenoviral infection, the in vivo production of mg/ml levels ExTek in rodents may be achieved for 7-10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, therefore, useful in treating such disorders, and in other situations of inappropriate neovascularization.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 tyrosine kinases. Certain compounds of this invention also inhibit the activity of additional tyrosine kinases such as Flt-1/VEGFR-1, Flt-4/VEGFR-3, Tie-1, Tie-2, FGFR, PDGFR, IGF-1R, c-Met, Src-subfamily kinases such as Lck, hck, fgr, Src, fyn, yes, etc. Additionally, some compounds of this invention significantly inhibit serine/threonine kinases such as PKC, MAP kinases, erk, CDKs, Plk-1, or Raf-1 which play an essential role in cell proliferation and cell-cycle progression. The potency and specificity of the generic compounds of this invention towards a particular protein kinase can often be altered and optimized by variations in the nature, number and arrangement of the substituents (i.e., $R_1$, $R_2$, $R_3$, A and ring 1) and conformational restrictions. In addition the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278-1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. In this manner, certain preferred compounds of this invention are, therefore, selective in their tyrosine kinase inhibitory activity.

In one embodiment, the present invention provides a method of treating a protein kinase-mediated condition in a patient, comprising administering to the patient a therapeutically or prophylactically effective amount of one or more compounds of formula (I).

A "protein kinase-mediated condition" or a "condition mediated by protein kinase activity" is a medical condition, such as a disease or other undesirable physical condition, the genesis or progression of which depends, at least in part, on the activity of at least one protein kinase. The protein kinase can be, for example, a protein tyrosine kinase or a protein serine/threonine kinase.

The patient to be treated can be any animal, and is preferably a mammal, such as a domesticated animal or a livestock animal. More preferably, the patient is a human.

A "therapeutically effective amount" is an amount of a compound of formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The method of the present invention is useful in the treatment of protein kinase-mediated conditions, such as any of the conditions described above. In one embodiment, the protein kinase-mediated condition is characterized by undesired angiogenesis, edema, or stromal deposition. For example, the condition can be one or more ulcers, such as ulcers caused by bacterial or fungal infections, Mooren ulcers and ulcerative colitis. The condition can also be due to a microbial infection, such as Lyme disease, sepsis, septic shock or infections by Herpes simplex, Herpes Zoster, human immunodeficiency virus, protozoa, toxoplasmosis or parapoxvirus; an angiogenic disorders, such as von Hippel Lindau disease, polycystic kidney disease, pemphigoid, Paget's disease and psoriasis; a reproductive condition, such as endometriosis, ovarian hyperstimulation syndrome, preeclampsia or menometrorrhagia; a fibrotic and edemic condition, such as sarcoidosis, fibrosis, cirrhosis, thyroiditis, hyperviscosity syndrome systemic, Osler-Weber-Rendu disease, chronic occlusive pulmonary disease, asthma, and edema following burns, trauma, radiation, stroke, hypoxia or ischemia; or an inflammatory/immunologic condition, such as systemic lupus, chronic inflammation, glomerulonephritis, synovitis, inflammatory bowel disease, Crohn's disease, rheumatoid arthritis, osteoarthritis, multiple sclerosis and graft rejection. Suitable protein kinase-mediated conditions also include sickle cell anaemia, osteoporosis, osteopetrosis, tumor-induced hypercalcemia and bone metastases. Additional protein kinase-mediated conditions which can be treated by the method of the present invention include ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease, in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, glioblastoma, hematopoietic malignancies, including leukaemia and lymphoma, tumor-induced pleural or pericardial effusions, and malignant ascites.

The compounds of the present invention are also useful in the treatment of pulmonary hypertension, especially in patients with thromboembolic disease (J Thorac Cardiovasc Surg, 2001, 122 (1), p. 65-73), Crow-Fukase (POEMS) syndrome and diabetic conditions such as glaucoma, diabetic retinopathy and microangiopathy.

The Src, Tec, Jak, Map, Csk, NFκB and Syk families of kinases play pivotal roles in the regulation of immune function. The Src family currently includes Fyn, Lck, Fgr, Fes, Lyn, Src, Yrk, Fyk, Yes, Hck, and Blk. The Syk family is currently understood to include only Zap and Syk. The TEC family includes Tec, Btk, Rlk and Itk. The Janus family of kinases is involved in the transduction of growth factor and proinflammatory cytokine signals through a number of receptors. Although BTK and ITK, members of the Tec family of kinases, play a less well understood role in immunobiology, their modulation by an inhibitor may prove therapeutically beneficial. The Csk family is currently understood to include Csk and Chk. The kinases RIP, IRAK-1, IRAK-2, NIK, p38 MAP kinases, Jnk, IKK-1 and IKK-2 are involved in the signal transduction pathways for key pro-inflammatory cytokines, such as TNF and IL-1. By virtue of their ability to inhibit one or more of these kinases, compounds of formula (I) may function as immunomodulatory agents useful for the maintenance of allografts, the treatment of autoimmune disorders and treatment of sepsis and septic shock. Through their ability to regulate the migration or activation of T cells, B-cells, mast cells, monocytes and neutrophils, these compounds could be used to treat such autoimmune diseases and sepsis. Prevention of transplant rejection, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula (I), through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the ltk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and themselves may become oncogenic by over-expression or mutation. By inhibiting the protein kinase activity of these proteins the disease process may be disrupted. Vascular restenosis may involve FGF and/or PDGF-promoted smooth muscle and endothelial cell proliferation. The ligand stimulation of FGFR, PDGFR, IGF1-R and c-Met in vivo is proangiogenic, and potentiates angiogenesis dependent disorders. Inhibition of FGFr, PDGFr, c-Met, or IGF1-R kinase activities individually or in combination may be an efficacious strategy for inhibiting these phenomena. Thus compounds of formula (I) which inhibit the kinase activity of normal or aberrant c-kit, c-met, c-fms, src-family members, EGFr, erbB2, erbB4, BCR-Abl, PDGFr, FGFr, IGF1-R and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie) are essential for the stimulation of endothelial cell growth, migration, organization, differentiation and the establishment of the requisite new functional vasculature. As a result of the vascular permeability factor activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and virally-encoded VEGF-E or HIV-Tat protein can also cause a vascular hyperpermeability response through the stimulation of a VEGFR kinase. KDR/VEGFR-2 and/or Tie-2 are expressed also in a select population of hematopoietic stem cells. Certain members of this population are pluripotent in nature and can be stimulated with growth factors to differentiate into endothelial cells and participate in vasculogenetic angiogenic processes. For this reason these have been called Endothelial Progenitor Cells (EPCs) (*J. Clin. Investig.* 103:1231-1236 (1999)). In some progenitors, Tie-2 may play a role in their recruitment, adhesion, regulation and differentiation (*Blood,* 4317-4326 (1997)). Certain agents according to formula (I) capable of blocking the kinase activity of endothelial cell specific kinases could therefore inhibit disease progression involving these situations.

Vascular destabilization of the antagonist ligand of Tie-2 (Ang2) is believed to induce an unstable "plastic" state in the endothelium. In the presence of high VEGF levels a robust angiogenic response may result; however, in the absence of VEGF or a VEGF-related stimulus, frank vessel regression and endothelial apoptosis can occur (Genes and Devel. 13: 1055-1066 (1999)). In an analogous manner a Tie-2 kinase inhibitor can be proangiogenic or antiangiogenic in the presence or absence of a VEGF-related stimulus, respectively.

The compounds of formula (I) or a salt thereof or pharmaceutical compositions containing a therapeutically effective amount thereof may be used in the treatment of protein kinase-mediated conditions, such as benign and neoplastic proliferative diseases and disorders of the immune system, as described above. For example, such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, acute lung injury and adult respiratory distress syndrome (ARDS).

The compounds of the present invention may also be useful in the prophylaxis of the above diseases.

It is envisaged that the disorders listed above are mediated to a significant extent by protein tyrosine kinase activity involving the VEGF receptors (e.g. KDR, Flt-1 and/or Tie-2). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula (I) as defined initially above for use as medicaments, particularly as inhibitors of protein kinase activity for example tyrosine kinase activity, serine kinase activity and threonine kinase activity. In yet another aspect the present invention provides the use of compounds of formula (I) as defined initially above in the manufacture of a medicament for use in the inhibition of protein kinase activity.

In this invention, the following definitions are applicable:

"Physiologically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

Pharmaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared from the following ingredients.

| | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinyl-pyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors and PI3 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formula (I) as a medicament.

A further aspect of the present invention provides the use of a compound of formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula (D) to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536-539) by a test compound relative to control.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the XbaI and NotI site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6$KDR(aa789-1354) were lysed by adding 50 ml of Triton X-100 lysis buffer (20 mM Tris, pH 8.0, 137 mM NaCl, 10% glycerol, 1% Triton X-100, 1 mM PMSF, 10 μg/ml aprotinin, 1 μg/ml leupeptin) to the cell pellet from 1 L of cell culture. The lysate was centrifuged at 19,000 rpm in a Sorval SS-34 rotor for 30 min at 4 EC. The cell lysate was applied to a 5 ml $NiCl_2$ chelating sepharose column, equilibrated with 50 mM HEPES, pH 7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH 7.5, 25 mM NaCl, 5 mM DTT buffer and stored at −80 EC.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL 1939 at the XbaI and NotI site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786-1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 μl) and the EGF ligand was acquired from Oncogene Research Products/Calbiochem (Cat # PF011-100).

Expression of ZAP70

The baculoviral expression vector used was pVL1393. (Pharmingen, Los Angeles, Calif.) The nucleotide sequence encoding amino acids M(H)6 $LVPR_9S$ was placed 5' to the region encoding the entirety of ZAP70 (amino acids 1-619). The nucleotide sequence encoding the ZAP70 coding region was generated through PCR using cDNA libraries isolated from Jurkat immortalized T-cells. The histidine residues enabled affinity purification of the protein (vide infra). The $LVPR_9S$ bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 μg/ml leupeptin, 10 μg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g. from Upstate Biotechnology Inc. (Saranac Lake, N.Y.) and Santa Cruz Biotechnology Inc. (Santa Cruz, Calif.)) or purified from known natural or recombinant sources using conventional methods.

Enzyme Linked Immunosorbent Assay (ELISA) for PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359-371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly($Glu_4$ Tyr), 20,000-50,000 MW) was employed together with ATP (typically 5 µM) at concentrations approximately twice the apparent Km in the assay.

The following procedure was used to assay the inhibitory effect of compounds of this invention on KDR, Flt-1, Flt-4, Tie-1, Tie-2, EGFR, FGFR, PDGFR, IGF-1-R, c-Met, Lck, hck, Blk, Csk, Src, Lyn, fgr, Fyn and ZAP70 tyrosine kinase activity:

Buffers and Solutions:
PGTPoly (Glu, Tyr) 4:1
Store powder at −20° C. Dissolve powder in phosphate buffered saline (PBS) for 50 mg/ml solution. Store ml aliquots at −20° C. When making plates dilute to 250 µg/ml in Gibco PBS.
Reaction Buffer: 100 mM Hepes, 20 mM $MgCl_2$, 4 mM $MnCl_2$, 5 mM DTT, 0.02% BSA, 200 µM $NaVO_4$, pH 7.10
ATP: Store aliquots of 100 mM at −20° C. Dilute to 20 µM in water
Washing Buffer: PBS with 0.1% Tween 20
Antibody Diluting Buffer: 0.1% bovine serum albumin (BSA) in PBS
TMB Substrate: mix TMB substrate and Peroxide solutions 9:1 just before use or use K-Blue Substrate from Neogen
Stop Solution: 1M Phosphoric Acid Procedure
1. Plate Preparation:
Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C. Wash 1× with 250 µl washing buffer and dry for about 2 hrs in 37° C. dry incubator.
Store coated plates in sealed bag at 4° C. until used.
2. Tyrosine Kinase Reaction:
Prepare inhibitor solutions at a 4× concentration in 20% DMSO in water.
Prepare reaction buffer
Prepare enzyme solution so that desired units are in 50 µl, e.g. for KDR make to 1 ng/µl for a total of 50 ng per well in the reactions. Store on ice.
Make 4×ATP solution to 20 µM from 100 mM stock in water. Store on ice.
Add 50 µl of the enzyme solution per well (typically 5-50 ng enzyme/well depending on the specific activity of the kinase)
Add 25 µl 4× inhibitor
Add 25 µl 4×ATP for inhibitor assay
Incubate for 10 minutes at room temperature
Stop reaction by adding 50 µl 0.05N HCl per well
Wash plate
**Final Concentrations for Reaction: 5 µM ATP, 5% DMSO
3. Antibody Binding
Dilute 1 mg/ml aliquot of PY20-HRP (Pierce) antibody (a phosphotyrosine antibody) to 50 ng/ml in 0.1% BSA in PBS by a 2 step dilution (100×, then 200×)
Add 100 µl Ab per well. Incubate 1 hr at room temp. Incubate 1 hr at 4 C.
Wash 4× plate
4. Color Reaction
Prepare TMB substrate and add 100 µl per well
Monitor OD at 650 nm until 0.6 is reached
Stop with 1M Phosphoric acid. Shake on plate reader.
Read OD immediately at 450 nm Optimal incubation times and enzyme reaction conditions vary slightly with enzyme preparations and are determined empirically for each lot.

For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

Compounds of formula (I) may have therapeutic utility in the treatment of diseases involving both identified, including those not mentioned herein, and as yet unidentified protein tyrosine kinases which are inhibited by compounds of formula (I).

Cdc2 Source
The human recombinant enzyme and assay buffer may be obtained commercially (New England Biolabs, Beverly, Mass. USA) or purified from known natural or recombinant sources using conventional methods.

Cdc2 Assay
A protocol that can be used is that provided with the purchased reagents with minor modifications. In brief, the reaction is carried out in a buffer consisting of 50 mM Tris pH 7.5, 100 mM NaCl, 1 mM EGTA, 2 mM DTT, 0.01% Brij, 5% DMSO and 10 mM $MgCl_2$ (commercial buffer) supplemented with fresh 300 µM ATP (31 µCi/ml) and 30 µg/ml histone type IIIss final concentrations. A reaction volume of 80 µL, containing units of enzyme, is run for 20 minutes at 25 degrees C. in the presence or absence of inhibitor. The reaction is terminated by the addition of 120 µL of 10% acetic acid. The substrate is separated from unincorporated label by spotting the mixture on phosphocellulose paper, followed by 3 washes of 5 minutes each with 75 mM phosphoric acid. Counts are measured by a betacounter in the presence of liquid scintillant.

PKC Kinase Source
The catalytic subunit of PKC may be obtained commercially (Calbiochem).

PKC Kinase Assay
A radioactive kinase assay is employed following a published procedure (Yasuda, I., Kirshimoto, A., Tanaka, S., Tominaga, M., Sakurai, A., Nishizuka, Y. *Biochemical and Biophysical Research Communication* 3:166, 1220-1227 (1990)). Briefly, all reactions are performed in a kinase buffer consisting of 50 mM Tris-HCl pH 7.5, 10 mM $MgCl_2$, 2 mM DTT, 1 mM EGTA, 100 µM ATP, 8 µM peptide, 5% DMSO and $^{33}$P ATP (8 Ci/mM). Compound and enzyme are mixed in the reaction vessel and the reaction is initiated by addition of the ATP and substrate mixture. Following termination of the reaction by the addition of 10 µL stop buffer (5 mM ATP in 75 mM phosphoric acid), a portion of the mixture is spotted on phosphocellulose filters. The spotted samples are washed 3 times in 75 mM phosphoric acid at room temperature for 5 to 15 minutes. Incorporation of radiolabel is quantified by liquid scintillation counting.

Erk2 Enzyme Source
The recombinant murine enzyme and assay buffer may be obtained commercially (New England Biolabs, Beverly Mass. USA) or purified from known natural or recombinant sources using conventional methods.

Erk2 Enzyme Assay
In brief, the reaction is carried out in a buffer consisting of 50 mM Tris pH 7.5, 1 mM EGTA, 2 mM DTT, 0.01% Brij, 5% DMSO and 10 mM $MgCl_2$ (commercial buffer) supplemented with fresh 100 µM ATP (31 µCi/ml) and 30 µM myelin basic protein under conditions recommended by the supplier. Reaction volumes and method of assaying incorporated radioactivity are as described for the PKC assay (vide supra).

In Vitro Models for T-Cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1-7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (2001 volume) in a U bottom microtiter plate (Costar Scientific). The cells are cultured in RPMI 1640 supplemented with either heat inactivated fetal bovine serum (Hyclone Laboratories) or pooled human AB serum from male donors, $5 \times 10^{-5}$M 2-mercaptoethanol and 0.5% DMSO, The cultures are pulsed with 0.5 μCi of $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-Vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 μg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α (TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 μg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6 \times 10^6$ per ml in tissue culture medium (RPMI 1640 supplemented with heat inactivated fetal bovine serum (Hyclone Laboratories) $5 \times 10^{-5}$M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560-2566, 1991; murine model: Lab. Invest. 4(3):278, 1981; rodent model: J. Immunol. 146(4): 1163-8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol: 142(7):2237-2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333-58, 1992; Transplantation: 57(12): 1701-17D6, 1994) or heart (Am. J. Anat.: 113:273, 1963). Briefly, full thickness skin grafts are transplanted from C57BL/6 mice to BALB/c mice. The grafts can be examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDRNVEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) can be purchased from Clonetics (San Diego, Calif.) and cultured according to the manufacturer directions. Only early passages (3-8) are used for this assay. Cells are cultured in 100 mm dishes (Falcon for tissue culture; Becton Dickinson; Plymouth, England) using complete EBM media (Clonetics).

2. For evaluating a compound's inhibitory activity, cells are trypsinized and seeded at $0.5$-$1.0 \times 10^5$ cells/well in each well of 6-well cluster plates (Costar; Cambridge, Mass.).

3. 3-4 days after seeding, plates are typically 90-100% confluent. Medium is removed from all the wells, cells are rinsed with 5-10 ml of PBS and incubated 18-24 h with 5 ml of EBM base media with no supplements added (i.e., serum starvation).

4. Serial dilutions of inhibitors are added in 1 ml of EBM media (25 μM, 5 μM, or 1 μM final concentration to cells and incubated for one hour at 37 C. Human recombinant VEGF$_{165}$ (R & D Systems) is then added to all the wells in 2 ml of EBM medium at a final concentration of 50 ng/ml and incubated at 37 C for 10 minutes. Control cells untreated or treated with VEGF only are used to assess background phosphorylation and phosphorylation induction by VEGF.

All wells are then rinsed with 5-10 ml of cold PBS containing 1 mM Sodium Orthovanadate (Sigma) and cells are lysed and scraped in 200 µl of RIPA buffer (50 mM Tris-HCl) pH 7, 150 mM NaCl, 1% NP-40, 0.25% sodium deoxycholate, 1 mM EDTA) containing protease inhibitors (PMSF 1 mM, aprotinin 1 µg/ml, pepstatin 1 µg/ml, leupeptin 1 µg/ml, Na vanadate 1 nM, Na fluoride 1 mM) and 1 µg/ml of Dnase (all chemicals from Sigma Chemical Company, St Louis, Mo.). The lysate is spun at 14,000 rpm for 30 min, to eliminate nuclei.

Equal amounts of proteins are then precipitated by addition of cold (-20 C) Ethanol (2 volumes) for a minimum of 1 hour or a maximum of overnight. Pellets are reconstituted in Laemli sample buffer containing 5%-mercaptoethanol (Bio-Rad; Hercules, Calif.) and boiled for 5 min. The proteins are resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins are probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4 C. After washing and incubating for 1 hour with HRP-conjugated F(ab)$_2$ of goat anti-rabbit or goat-anti-mouse IgG the bands are visualized using the emission chemiluminescence (ECL) system (Amersham Life Sciences, Arlington Height, Ill.).

In Vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829-837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema. Materials: All hormones can be purchased from Sigma (St. Louis, Mo.) or Cal Biochem (La Jolla, Calif.) as lyophilized powders and prepared according to supplier instructions. Vehicle components (DMSO, Cremaphor EL) can be purchased from Sigma (St. Louis, Mo.). Mice (Balb/c, 8-12 weeks old) can be purchased from Taconic (Germantown, N.Y.) and housed in a pathogen-free animal facility in accordance with institutional Animal Care and Use Committee Guidelines.

Method:

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p.

Day 4: Mice are randomized and divided into groups of 5-10. Test compounds are administered by i.p., i.v. or p.o. routes depending on solubility and vehicle at doses ranging from 1-100 mg/kg. Vehicle control group receive vehicle only and two groups are left untreated.

Thirty minutes later, experimental, vehicle and 1 of the untreated groups are given an i.p. injection of 17-estradiol (500 µg/kg). After 2-3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test. Non-stimulated control group is used to monitor estradiol response.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519-528; Anat. Rec. (1997), 249(1), 63-73; Int. J. Cancer (1995), 63(5), 694-701; Vasc. Biol. (1995), 15(11), 1857-6). The model preferably runs over 3-4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

The teachings of all references, including journal articles, patents and published patent applications, are incorporated herein by reference in their entirety.

The following examples are for illustrative purposes and are not to be construed as limiting the scope of the present invention.

Preparation 1

4-Nitro-1H-5-pyrazolecarboxamide

A suspension of 4-nitro-1H-5-pyrazolocarboxylic acid (10.0 g, 64 mmol) in dichloromethane (150 mL) was treated with oxalyl chloride (8.9 g, 71 mmol) and a few drops of N,N-dimethylformamide. The mixture was stirred at ambient temperature for 18 hours. The solvent was removed under reduced pressure then the residue was dissolved in acetone (40 mL). The solution was cooled in an ice bath then a solution of 30% aqueous ammonium hydroxide (60 mL) was added slowly while maintaining the temperature of the mixture below 10° C. The mixture was warmed to ambient temperature then diluted with water (60 mL). The acetone was removed by evaporation under reduced pressure and the resulting slurry was cooled in an ice bath then the precipitate was collected by filtration and washed with water. The material thus collected was dried under high vacuum to yield the title compound (9 g, 90%) as a white solid: $^1$H NMR (DMSO-d$_6$, 400 MHz) δ 14.1 (bs, 1H), 8.70 (s, 1H), 8.05 (s, 1H), 7.82 (s, 1H); RP-HPLC (Hypersil HS C18, 5 µm, 100 A, 250×4.6 mm; 5%-100% acetonitrile-0.05 M ammonium acetate over 25 min, 1 mL/min) t$_r$ 5.82 min; MS: MH$^+$ 157.1

Preparation 2

4-Nitro-1H-5-pyrazolecarbonitrile

A suspension of 4-nitro-1H-5-pyrazolecarboxamide (7.80 g, 50 mmol) in dichloromethane (300 mL) and pyridine (30 mL) was treated with a solution of phosgene in toluene (20%, 50 mL). The mixture was stirred for 16 hours at ambient temperature then water (20 mL) was slowly added to the mixture, followed by 6 N aqueous hydrochloric acid (50 mL) and brine (15 mL). The mixture was extracted with dichloromethane (5×50 mL) and ethyl acetate (3×50 mL). The organic solutions were combined and dried over magnesium sulfate, filtered and the filtrate concentrated to a volume of about 150 mL then it was extracted with 1N aqueous hydrochloric acid (25 mL) and then brine (15 mL). The organic layer was dried over magnesium sulfate then filtered and the filtrate concentrated under reduced pressure to yield the title compound as a tan solid (6.36 g, 92%): $^1$H NMR (DMSO-$d_6$, 400 MHz) δ 14.99 bs, 1H), 9.15 (s, 1H); RP-HPLC (Hypersil HS C18, 5 μm, 100 A, 250×4.6 mm; 5%-100% acetonitrile-0.05 M ammonium acetate over 25 min, 1 mL/min) $t_r$ 12.05 min; MS: MH$^+$ 137.0

Preparation 3

1H-Pyrazolo[4,3-d]pyrimidin-7-amine

4-Nitro-1H-5-pyrazolecarbonitrile (6.25 g, 45.3 mmol) in ethanol (100 mL) was treated with 10% Palladium on carbon (0.50 g) and hydrogenated in a Parr shaker at 50 psi for 18 hours. The catalyst was removed by filtration through a pad of diatomaceous earth. The filtrate was then treated with formamidine acetate (37.7 g, 0.363 mol) then the mixture was heated at reflux for one hour. The mixture was cooled and then approximately 50 mL of the solvent was removed under reduced pressure. The precipitate which formed was isolated by filtration and washed with ethyl acetate (3×25 mL) then discarded. The filtrate was concentrated under reduced pressure to a volume of approximately 40 mL. The mixture was heated to dissolve all of the material then applied to a silica gel column which was eluted with ethyl acetate/methanol (8:2). The appropriate fractions were concentrated to give the title compound (3.85 g, 61%) which contained 18% formamidine acetate by weight as determined by $^1$H NMR: $^1$H NMR (DMSO-$d_6$, 400 MHz) δ 13.3 bs, 1H), 8.15 (s, 1H) 8.07 (s, 1H), 7.47 (bs, 2H); RP-HPLC (Hypersil HS C18, 5 μm, 100 A, 250×4.6 mm; 5%-100% acetonitrile-0.05 M ammonium acetate over 25 min, 1 mL/min) $t_r$ 4.95 min; MS: MH$^+$ 136.1, M–H$^+$ 134.1

Preparation 4

3-Iodo-1H-pyrazolo[4,3-d]pyridin-7-amine

1H-Pyrazolo[4,3-d]pyrimidin-7-amine (82% pure, 2.85 g, 17.3 mmol) in N,N-dimethylformamide (40 mL) was treated with N-iodosuccinimide (3.8 g, 16.9 mmol). The mixture was heated in an 80° C. oil bath for 1.5 hours then cooled and concentrated under reduced pressure. Ethanol (20 mL) and water (10 mL) was added to the residue then stirred and cooled in an ice bath. The precipitate was collected by filtration and washed with water. The filtrate was concentrated under reduced pressure then water (20 mL) was added and the solid was again collected by filtration and washed with water. The solids thus isolated were combined and dried under high vacuum to give the desired title compound as a brown powder: $^1$H NMR (DMSO-$d_6$, 400 MHz) δ 13.2 (s, 1H), 8.21 (s, 1H), 7.39 (bs, 2H); RP-HPLC (Hypersil HS C18, 5 μm, 100 A, 250×4.6 mm; 5%-100% acetonitrile-0.05 M ammonium acetate over 25 min, 1 mL/min) $t_r$ 8.58 min; MS: MH$^+$ 262.0, M–H$^+$ 259.9

Preparation 5

4-Fluoro-2-methoxy-1-nitrobenzene

A mixture of 5-fluoro-2-nitrophenol (3.0 g, 19.1 mmol), potassium carbonate (2.50 g, 21.0 mmol) and dimethyl sulfate (2.65 g, 21.0 mmol) in acetone was stirred at ambient temperature for 24 hours. The solvents were removed under reduced pressure and then water (30 mL) and dichloromethane (30 mL) was added to the residue. The combined organics solutions were dried over magnesium sulfate then filtered and the filtrate concentrated under reduced pressure to provide an oil. This was purified by flash chromatography on silica gel using dichloromethane/heptane (7:3) as an eluent to provide the title compound as a crystalline solid (3.24 g, 100%): $^1$H NMR (CDCl$_3$, 400 MHz) δ 7.96 (M, 1H), 6.80 (m, 1H), 6.73 (m, 1H), 3.96 (s, 3H); RP-HPLC (Hypersil HS C18, 5 μm, 100 A, 250×4.6 mm; 5%-100% acetonitrile-0.05 M ammonium acetate over 25 min, 1 μL/min) $t_r$ 17.82 min; MS: MH$^+$ 172.2

Preparation 6 tert-Butyl 4{[(trifluoromethyl)sulfonyl]oxy}-1,2,3,6-tetrahydro-1-pyridinecarboxylate The title compound was synthesized according to the method disclosed in Wustrow, D. J., Wise, L. D., Synthesis, 1991, pg 993-995, which is incorporated herein by reference in its entirety.

Preparation 7 tert-Butyl 4-(4,4,5,5-tetramethyl-1,3,2-dioxaborolan-2-yl)-1,2,3,6-tetrahydro-1-pyridinecarboxylate A mixture of tert-butyl 4{[(trifluoromethyl)sulfonyl]oxy}-1,2,3,6-tetrahydro-1-pyridinecarboxylate (1.8 g, 2.42 mmol), pinacol diboron (1.4 g, 5.44 mmol), potassium acetate (1.6 g, 16.32 mmol) and [1,1'-bis(diphenylphosphino)ferrocene]dichloropalladium(II) complex with dichloromethane (0.27 g, 0.33 mmol) in N,N-dimethylformamide (30 mL) was heated in an 85° C. oil bath for 17 hours. The solvent was evaporated under reduced pressure then the residue was triturated with dichloromethane (30 mL). The mixture was filtered through a bed of diatomaceous earth then the solvents were evaporated under reduced pressure and the residue purified by flash chromatography on silica gel with heptane/ethyl acetate (8:2) as an eluent. The appropriate fractions were concentrated under reduced pressure to provide the title compound as a crystalline solid (0.87 g, 52%); TLC $R_F$ 0.44, heptane/ethyl acetate (8:2), visualized by PMA/heat, Silica Gel 60 F$_{254}$ plates; $^1$H NMR (CDCl$_3$, 400 MHz) δ 6.46 (m, 1H), 3.94 (m, 2H), 3.43 (m, 2H), 2.21 (m, 2H), 1.45 (s, 9H), 1.26 (s, 12H)

Preparation 8

3-Iodo-1-(3-methoxy-4-nitrophenyl)-1H-pyrazolo[4,3-d]pyrimidin-7-amine

A mixture of 3-iodo-1H-pyrazolo[4,3-d]pyrimidin-7-amine (500 mg, 1.92 mmol) and 4-fluoro-2-methoxy-1-nitrobenzene (360 mg, 2.11 mmol) in N,N-dimethylformamide (5 mL) was treated with 60% sodium hydride in oil (92 mg, 2.30 mmol) then heated in an 85° C. oil bath for 17 hours. The solvent was removed by evaporation under reduced pressure then the residue was dissolved in a minimum of hot N,N-dimethylformamide and applied to a silica gel column and eluted with ethyl acetate to provide the title compound (405 mg, 51%) as a yellow solid after concentration of the appropriate fractions: $^1$H NMR (DMSO-$d_6$, 400 MHz) δ 8.38 (s, 1H), 8.10 (d, 1H), 7.47 (s, 1H), 7.30 (m, 1H), 7.15 (bs, 2H), 3.98 (s, 3H); RP-HPLC (Hypersil HS C18, 5 μm, 100 A, 250×4.6 mm; 5%-100% acetonitrile-0.05 M ammonium acetate over 25 min, 1 mL/min) $t_r$ 16.17 min; MS: MH$^+$ 413.1, M–H$^+$ 411.1

Preparation 9 tert-Butyl 4-[7-amino-1-(3-methoxy-4-nitrophenyl)-1H-pyrazolo[4,3-d]pyrimidin-3-yl]-1,2,3,6-tetrahydro-1-pyridinecarboxylate A mixture of 3-iodo-1-(3-methoxy-4-nitrophenyl)-1H-pyrazolo[4,3-d]pyrimidin-7-amine (300 mg, 0.728 mmol), tert-butyl 4-(4,4,5,5-tetramethyl-1,3,2-dioxaborolan-2-yl)-1,2,3,6-tetrahydro-1-pyridinecarboxylate (270 mg, 0.874 mmol), sodium carbonate (185 mg, 1.75 mmol) and tetrakis(triphenylphosphine)palladium(0) (50 mg, 0.044 mmol) in 1,2-dimethoxyethane (6 mL) and water (3 mL) was heated in an 85° C. oil bath for 1.75 hours. tert-Butyl 4-(4,4,5,5-tetramethyl-1,3,2-dioxaborolan-2-yl)-1,2,3,6-tetrahydro-1-pyridinecarboxylate (45 mg, 0.146 mmol) was added to the mixture and then it was heated in the 85° C. oil bath for another 16 hours. The solvents were evaporated under reduced pressure then the residue was partitioned between water (10 mL) and ethyl acetate (15 mL). The layers were separated and then the aqueous layer was extracted with ethyl acetate (10 mL), dichloromethane (20 mL) and then a 10% solution of methanol in dichloromethane (20 mL). The organic solutions thus obtained were combined and evaporated to a residue which was purified by flash chromatography on silica gel using ethyl acetate as an eluent to provide the title compound as a yellow solid (205 mg, 60%): $^1$H NMR (DMSO-$d_6$, 400 MHz) δ 8.40 (s, 1H), 8.10 (d, 1H), 7.50 (m, 1H), 7.42 (s, 1H), 7.31 (d, 1H), 7.1 (bs, 2H), 4.13 (m, 2H), 3.99 (s, 3H), 3.58 (m, 2H), 2.67 (m, 2H), 1.44 (s, 9H) RP-HPLC (Hypersil HS C18, 5 μm, 100 A, 250×4.6 mm; 5%-100% acetonitrile-0.05 M ammonium acetate over 25 min, 1 mL/min) $t_r$ 21.42 min; MS: M–H$^+$ 466.3

Preparation 10 tert-Butyl 4-[7-amino-1-(4-amino-3-methoxyphenyl)-1H-pyrazolo[4,3-d]pyrimidin-3-yl]-1-piperidinecarboxylate A mixture of tert-butyl 4-[7-amino-1-(3-methoxy-4-nitrophenyl)-1H-pyrazolo[4,3-d]pyrimidin-3-yl]-1,2,3,6-tetrahydro-1-pyridinecarboxylate (200 mg, 0.428 mmol) and 10% palladium on carbon (100 mg) in methanol (20 mL) and hydrogenated in a Parr shaker at 55 psi for 18 hours. The catalyst was removed by filtration through a pad of diatomaceous earth and the filtrate concentrated under reduced pressure then the residue was dissolved methanol (20 mL). Platinum (IV) oxide (100 mg) was added and the mixture was hydrogenated in a Parr shaker at 55 psi for 30 hours. The catalyst was removed by filtration through a pad of diatomaceous earth and the filtrate concentrated under reduced pressure to provide the title compound as a brown solid (175 mg, 93%): $^1$H NMR (DMSO-$d_6$, 400 MHz) δ 8.22 (s, 1H), 6.96 (d, 1H), 6.84 (d, 1H), 6.74 (d, 1H), 6.5 (bs, 2H), 5.75 (bs, 2H), 4.03 (m, 2H), 3.76 (s, 3H), 3.22 (m, 1H), 2.93 (m, 2H), 1.7-2.1 (m, 4H), 1.42 (s, 9H) RP-HPLC (Hypersil HS C18, 5 μm, 100 A, 250×4.6 mm; 5%-100% acetonitrile-0.05 M ammonium acetate over 25 min, 1 mL/min) $t_r$ 16.93 min; MS: MH$^+$ 440.2

Example 1

N2-{4-[7-Amino-3-(4-piperidyl)-1H-pyrazolo[4,3-d]pyrimidin-1-yl]-2-methoxyphenyl}-1-methyl-1H-2-indolecarboxamide tert-Butyl 4-[7-amino-1-(4-amino-3-methoxyphenyl)-1H-pyrazolo[4,3-d]pyrimidin-3-yl]-1-piperidinecarboxylate (75 mg, 0.171 mmol) was dissolved in dichloromethane (5 mL) and pyridine (0.5 mL) then the mixture was cooled to 5° C. in an ice bath. 1-Methylindole carbonyl chloride (0.188 mmol) in dichloromethane (1 mL) was added then the mixture was stirred for 10 minutes. The solvents were removed by evaporation under reduced pressure then the residue was dissolved in acetone (3 mL) and 6 N aqueous hydrochloric acid (6 mL). The mixture was heated in an 85° C. oil bath for 1 hour. The solvents were removed under reduced pressure and the material purified by preparative reverse phase chromatography. Lyophilization afforded a white powder (65 mg) which was treated with dichloromethane (25 mL) and 5 N aqueous sodium hydroxide (10 mL). The layers were separated and then the aqueous layer was extracted with dichloromethane (2×10 mL). The organic solutions were combined and dried over magnesium sulfate then filtered. The filtrate was concentrated to give the title compound (30 mg) as a white solid: $^1$H NMR (DMSO-$d_6$, 400 MHz) δ 9.48 (s, 1H), 8.29 (s, 1H), 8.10 (d, 1H), 7.71 (d, 1H), 7.58 (d, 1H), 7.36 (m, 2H), 7.27 (s, 1H), 7.15 (m, 2H), 6.59 (bs, 2H), 4.04 (s, 3H), 3.89 (s, 3H), 3.19 (m, 1H), 3.07 (m, 2H), 2.63 (m, 2H), 1.87 (m, 4H); RP-HPLC (Hypersil HS C18, 5 μm, 100 A, 250×4.6 mm; 5%-100% acetonitrile-0.05 M ammonium acetate over 25 min, 1 mL/min) $t_r$ 15.03 min; MS: MH$^+$ 497.3, M–H$^+$ 495.2

Example 2

N2-{4-[7-Amino-3-(4-piperidyl)-1H-pyrazolo[4,3-d]pyrimidin-1-yl]-2-methoxyphenyl}-2-fluoro-4-(trifluoromethyl)benzamide The title compound (25 mg) was prepared from tert-Butyl 4-[7-amino-1-(4-amino-3-methoxyphenyl)-1H-pyrazolo[4,3-d]pyrimidin-3-yl]-1-piperidinecarboxylate (75 mg, 0.171 mmol) and 2-fluoro-4-(trifluoromethyl)benzoyl chloride in the manner described for the preparation of N2-{4-[7-amino-3-(4-piperidyl)-1H-pyrazolo[4,3-d]pyrimidin-1-yl]-2-methoxyphenyl}-1-methyl-1H-2-indolecarboxamide: $^1$H NMR (DMSO-$d_6$, 400 MHz) δ 9.94 (bs, 1H), 8.29 (m, 2H), 7.98 (t, 1H), 7.90 (d, 1H), 7.74 (d, 1H), 7.26 (d, 1H), 7.15 (m, 1H), 6.6 (bs, 2H), 3.93 (s, 3H), 3.18 (m, 1H), 3.06 (m, 2H), 2.66 (m, 2H), 1.87-1.97 (m, 4H); RP-HPLC (Hypersil HS C18, 5 μm, 100 A, 250×4.6 mm; 5%-100% acetonitrile-0.05 M ammonium acetate over 25 min, 1 mL/min) $t_r$ 15.38 min; MS: MH$^+$ 530.2, M–H$^+$ 528.2

Example 3

1-(4-Amino-3-methoxyphenyl)-3-iodo-1H-pirazolo [4,3-d]pyrimidin-7-amine

3-Iodo-1-(3-methoxy-4-nitrophenyl)-1H-pyrazolo[4,3-d] pyrimidin-7-amine (300 mg, 0.728 mmol) in ethanol (10 mL) and water (5 mL) was heated in an 80° C. oil bath then sodium dithionite (635 mg, 3.64 mmol) was added. After 18 hours the solvents were removed by evaporation under reduced pressure and the material was purified by preparative reverse phase chromatography. Lyophilization afforded 135 mg of material which was dissolved in N,N-dimethylformamide and applied to a column of basic ion exchange resin and eluted with methanol. The eluent was concentrated under reduced pressure to provide the title compound (80 mg): $^1$H NMR (DMSO-$d_6$, 400 MHz) δ 8.28 (s, 1H), 7.01 (s, 1H), 6.96 (d, 1H), 6.76 (d, 1H), 5.28 (bs, 2H), 3.80 (s, 3H); RP-HPLC (Hypersil HS C18, 5 μm, 100 A, 250×4.6 mm; 5%-100% acetonitrile-0.05 M ammonium acetate over 25 min, 1 mL/min) $t_r$ 13.08 min; MS: MH$^+$ 383.1

Example 4

N1-[4-(7-Amino-1H-pyrazolo[4,3-d]pyrimidin-1-yl)-2-Methoxyphenyl]-2-fluoro-4-(trifluoromethyl)benzamide acetate 1-(4-Amino-3-methoxyphenyl)-3-iodo-1H-pyrazolo[4,3-d]pyrimidin-7-amine (80 mg, 0.209 mmol) in dichloromethane (5 mL) and pyridine (0.5 mL) was cooled to 5° C. in an ice bath then 2-fluoro-4-(trifluoromethyl)benzoyl chloride (52 mg, 0.230 mmol) was added dropwise. The solution was warmed to ambient temperature for 30 minutes then the solvents were removed by evaporation. The residue was dissolved in methanol (10 mL), 10% palladium on carbon (50 mg) was added and the mixture was hydrogenated at atmospheric pressure and 60° C. for 1 hour. The catalyst was removed by filtration through a pad of diatomaceous earth then the filtrate was concentrated and the material purified by preparative reverse phase chromatography. Lyophilization yielded the title compound (25 mg) as a white solid: $^1$H NMR (DMSO-$d_6$, 400 MHz) δ 9.98 (s, 1H), 8.32 (m, 3H), 7.99 (t, 1H), 7.89 (d, 1H), 7.75 (d, 1H), 7.32 (d, 1H), 7.18 (m, 1H), 6.7 (bs, 2H), 3.93 (s, 3H), 1.60 (s, 3H); RP-HPLC (Hypersil HS C18, 5 μm, 100 A, 250×4.6 mm; 5%-100% acetonitrile-0.05 M ammonium acetate over 25 min, 1 mL/min) $t_r$ 18.75 min; MS: MH$^+$ 447.1, M–H$^+$ 445.1

Example 5

N1-{4-[7-Amino-3-(4-piperidyl)-1H-pyrazolo[4,3-d]pyrimidin-1-yl]-2-methoxyphenyl}-1-benzenesulfonamide bisacetate The title compound was prepared from tert-Butyl 4-[7-amino-1-(4-amino-3-methoxyphenyl)-1H-pyrazolo[4,3-d]pyrimidin-3-yl]-1-piperidinecarboxylate and benzenesulfonyl chloride in the manner described for the preparation of N2-{4-[7-amino-3-(4-piperidyl)-1H-pyrazolo[4,3-d]pyrimidin-1-yl]-2-methoxyphenyl}-1-methyl-1H-2-indolecarboxamide: $^1$H NMR (DMSO-$d_6$, 400 MHz) δ 8.2 (s, 1H), 7.73 (m, 2H), 7.38 (m, 3H), 7.12 (d, 1H), 6.80 (s, 1H), 6.68 (m, 1H), 3.67 (s, 3H), 3.15 (m, 2H), 2.69 (m, 2H), 1.7-2.0 (m, 13H); RP-HPLC (Hypersil HS C18, 5 μm, 100 A, 250×4.6 mm; 5%-100% acetonitrile-0.05 M ammonium acetate over 25 min, 1 mL/min) $t_r$ 11.93 min; MS: MH$^+$ 480.2, M–H$^+$ 378.1

Example 6

Benzyl N-{4-[7-amino-3-(4-piperidyl)-1H-pyrazolo [4,3-d]pyrimidin-1-yl]-2-methoxyphenyl}carbamate bisacetate The title compound was prepared from tert-Butyl 4-[7-amino-1-(4-amino-3-methoxyphenyl)-1H-pyrazolo[4,3-d]pyrimidin-3-yl]-1-piperidinecarboxylate and benzyl chloroformate in the manner described for the preparation of N2-{4-[7-amino-3-(4-piperidyl)-1H-pyrazolo[4,3-d]pyrimidin-1-yl]-2-methoxyphenyl}-1-methyl-1H-2-indolecarboxamide: $^1$H NMR (DMSO-$d_6$, 400 MHz) δ 8.9 (bs, 1H), 8.27 (s, 1H), 7.89 (d, 1H), 7.3-7.4 (m, 5H), 7.17 (s, 1H), 7.06 (d, 1H), 6.6 (bs, 2H), 5.18 (s, 2H), 3.86 (s, 3H), 3.18 (m, 1H), 3.08 (m, 2H), 2.69 (m, 2H), 1.87-1.98 (m, 2H), 1.76 (s, 6H); RP-HPLC (Hypersil HS C18, 5 μm, 100 A, 250×4.6 mm; 5%-100% acetonitrile-0.05 M ammonium acetate over 25 min, 1 mL/min) $t_r$ 14.27 min; MS: MH$^+$ 474.2, M–H$^+$ 472.2

Example 7

N-{4-[7-Amino-3-(4-piperidyl)-1H-pyrazolo[4,3-d] pyrimidin-1-yl]-2-methoxyphenyl}-N-phenylurea The title compound was prepared from tert-Butyl 4-[7-amino-1-(4-amino-3-methoxyphenyl)-1H-pyrazolo[4,3-d]pyrimidin-3-yl]-1-piperidinecarboxylate and phenyl isocyanate in the manner described for the preparation of N2-{4-[7-amino-3-(4-piperidyl)-1H-pyrazolo[4,3-d]pyrimidin-1-yl]-2-methoxyphenyl}-1-methyl-1H-2-indolecarboxamide: $^1$H NMR (DMSO-$d_6$, 400 MHz) δ 9.40 (s, 1H), 8.44 (s, 1H), 8.33 (d, 1H), 8.23 (s, 1H), 7.47 (d, 2H), 7.31 (m, 2H), 7.19 (s, 1H), 7.06 (m, 1H), 7.00 (m, 1H), 6.5 (bs, 2H), 3.95 (s, 3H), 3-3.2 (m, 3H), 2.71 (m, 2H), 1.9-2.0 (m, 4H); RP-HPLC (Hypersil HS C18, 5 μm, 100 A, 250×4.6 mm; 5%-100% acetonitrile-0.05 M ammonium acetate over 25 min, 1 mL/min) $t_r$ 13.02 min; MS: MH$^+$ 459.1, M–H$^+$ 457.2

Example 8

N2-{4-[7-Amino-3-(1-tetrahydro-2H-4-pyranyl-4-piperidyl)-1H-pyrazolo[4,3-d]pyrimidin-1-yl]-2-methoxyphenyl}-1-methyl-1H-2-indolecarboxamide maleate A mixture of N2-{4-[7-amino-3-(4-piperidyl)-1H-pyrazolo[4,3-d]pyrimidin-1-yl]-2-methoxyphenyl}-1-methyl-1H-2-indolecarboxamide (320 mg, 0.645 mmol), tetrahydro-4H-pyran-4-one (129 mg, 1.29 mmol) and sodium triacetoxyborohydride (275 mg, 1.29 mmol) in 1,2-dichloroethane (15 mL) was heated at 75° C. for 3 hours. The mixture was treated with saturated aqueous sodium bicarbonate (20 mL) and the layers were separated. The aqueous layer was extracted with dichloromethane (3×20 mL) then the combined organic solutions were dried over magnesium sulfate, filtered and the filtrate concentrated under reduced pressure. The residue was purified by flash chromatography on silica gel then the material (190 mg) was heated to reflux in a mixture of ethyl acetate (10 mL) and ethanol (1 mL). Maleic acid (85 mg) in ethyl acetate (4 mL) was added to the mixture, which was then heated at reflux for 30 min. The mixture was cooled to ambient temperature then the solid was collected by filtration to yield the title compound (220 mg): $^1$H NMR (DMSO-$d_6$, 400 MHz) δ 9.49 (s, 1H), 9.15 (bs, 1H), 8.33 (s, 1H), 8.13 (d, 1H), 7.71 (d, 1H), 7.59 (d, 1H), 7.35 (m, 3H), 7.28 (s, 1H), 7.16 (m, 2H), 6.8 (bs, 2H), 6.02 (s, 2H), 4.04 (s, 3H), 3.99 (m, 1H), 3.94 (s, 1H), 3.2-3.6 (m, 8H), 2.31 (m, 4H), 2.0 (m, 2H), 1.70 (m, 2H); RP-HPLC (Hypersil HS C18, 5 μm, 100 A, 250×4.6 mm; 5%-100% acetonitrile-0.05 M ammonium acetate over 25 min, 1 mL/min) $t_r$ 15.63 min; MS: MH$^+$ 581.2, M–H$^+$ 579.2

Example 9

N2-{4-[7-amino-3-(1-ethyl-4-piperidyl)-1H-pyrazolo[4,3-d]pyrimidin-1-yl]-2-methoxyphenyl}-1-methyl-1H-2-indolecarboxamide maleate The title compound was prepared from N2-{4-[7-amino-3-(4-piperidyl)-1H-pyrazolo[4,3-d]pyrimidin-1-yl]-2-methoxyphenyl}-1-methyl-1H-2-indolecarboxamide and acetaldehyde in the manner described for the preparation N2-{4-[7-amino-3-(1-tetrahydro-2H-4-pyranyl-4-piperidyl)-1H-pyrazolo[4,3-d]pyrimidin-1-yl]-2-methoxyphenyl}-1-methyl-1H-2-indolecarboxamide maleate: $^1$H NMR (DMSO-d$_6$, 400 MHz) δ 9.49 (s, 1H), 9.10 (bs, 1H), 8.33 (s, 1H), 8.13 (d, 1H), 7.71 (d, 1H), 7.59 (d, 1H), 7.28-7.35 (m, 3H), 7.15 (m, 2H), 6.80 (bs, 2H), 6.01 (s, 2H), 4.04 (s, 3H), 3.94 (s, 3H), 3.62 (m, 2H), 3.38 (m, 1H), 3.16 (m, 4H), 2.26 (m, 4H), 1.27 (t, 3H); RP-HPLC (Hypersil HS C18, 5 μm, 100 A, 250×4.6 mm; 5%-100% acetonitrile-0.05 M ammonium acetate over 25 min, 1 mL/min) $t_r$ 15.77 min; MS: MH$^+$ 525.0, M–H$^+$ 523.0

Preparation 11

3-Iodo-1-(4-nitrophenyl)-1H-pyrazolo[4,3-d]pyrimidin-7-amine

The title compound was prepared from 3-iodo-1H-pyrazolo[4,3-d]pyrimidin-7-amine and 1-fluoro-4-nitrobenzene as described for the preparation of 3-iodo-1-(3-methoxy-4-nitrophenyl)-1H-pyrazolo[4,3-d]pyrimidin-7-amine $^1$H NMR (DMSO-d$_6$, 400 MHz) δ 8.40-8.50 (m, 3H), 7.79 (d, 2H), 7.11 (bs, 2H); RP-HPLC (Hypersil HS C18, 5 μm, 100 A, 250×4.6 mm; 5%-100% acetonitrile-0.05 M ammonium acetate over 25 min, 1 mL/min) $t_r$ 15.98 min

Preparation 12 tert-Butyl 4-[7-amino-1-(4-nitrophenyl)-1H-pyrazolo[4,3-d]pyrimidine-3-yl]-1,2,3,6-tetrahydro-1-pyridinecarboxylate The title compound was prepared from 3-iodo-1-(4-nitrophenyl)-1H-pyrazolo[4,3-d]pyrimidin-7-amine and tert-butyl 4-(4,4,5,5-tetramethyl-1,3,2-dioxaborolan-2-yl)-1,2,3,6-tetrahydro-1-pyridinecarboxylate in the manner described for the preparation of tert-butyl 4-[7-amino-1-(3-methoxy-4-nitrophenyl)-1H-pyrazolo[4,3-d]pyrimidin-3-yl]-1,2,3,6-tetrahydro-1-pyridinecarboxylate: $^1$H NMR (DMSO-d$_6$, 400 MHz) δ 8.44 (m, 3H), 7.76 (d, 2H), 7.53 (m, 1H), 7.05 (bs, 2H), 4.13 (m, 2H), 3.58 (m, 2H), 2.67 (m, 2H), 1.44 (s, 9H); RP-HPLC (Hypersil HS C18, 5 μm, 100 A, 250×4.6 mm; 5%-100% acetonitrile-0.05 M ammonium acetate over 25 min, 1 mL/min) $t_r$ 21.70 min; MS: MH$^+$ 438.1, M–H$^+$ 436.1

Preparation 13 tert-Butyl 4-[7-amino-1-(4-aminophenyl)-1H-pyrazolo[4,3-d]pyrimidine-3-yl]-1-piperidinecarboxylate The title compound was prepared from tert-butyl 4-[7-amino-1-(4-nitrophenyl)-1H-pyrazolo[4,3-d]pyrimidine-3-yl]-1,2,3,6-tetrahydro-1-pyridinecarboxylate in the same manner as described for the preparation of tert-butyl 4-[7-amino-1-(4-amino-3-methoxyphenyl)-1H-pyrazolo[4,3-d]pyrimidin-3-yl]-1-piperidinecarboxylate: RP-HPLC (Hypersil HS C18, 5 μm, 100 A, 250×4.6 mm; 5%-100% acetonitrile-0.05 M ammonium acetate over 25 min, 1 mL/min) $t_r$ 16.07 min; MS: MH$^+$ 410.2

Example 10

N1-{4-[7-Amino-3-(4-piperidyl)-1H-pyrazolo[4,3-d]pyrimidin-1-yl]phenyl}-1-benzenesulfonamide bisacetate The title compound was prepared from tert-butyl 4-[7-amino-1-(4-aminophenyl)-1H-pyrazolo[4,3-d]pyrimidine-3-yl]-1-piperidinecarboxylate and benzenesulfonyl chloride in the manner described for the preparation of N2-{4-[7-amino-3-(4-piperidyl)-1H-pyrazolo[4,3-d]pyrimidin-1-yl]-2-methoxyphenyl}-1-methyl-1H-2-indolecarboxamide: $^1$H NMR (DMSO-d$_6$, 400 MHz) δ 8.22 (s, 1H), 7.75 (m, 2H), 7.45 (m, 3H), 7.14 (d, 2H), 7.02 (d, 2H), 6.5 (bs, 1H), 3.0-3.3 (m, 3H), 2.77 (m, 2H), 2.0 (m, 4H), 1.89 (s, 6H); RP-HPLC (Hypersil HS C18, 5 μm, 100 A, 250×4.6 mm; 5%-100% acetonitrile-0.05 M ammonium acetate over 25 min, 1 mL/min) $t_r$ 11.63 min; MS: MH$^+$ 450.0, M–H$^+$ 448.0

Example 11

N2-{4-[7-Amino-3-(4-piperidyl)-1H-pyrazolo[4,3-d]pyrimidin-1-yl]phenyl}-1-methyl-1H-2-indolecarboxamide The title compound was prepared from tert-butyl 4-[7-amino-1-(4-aminophenyl)-1H-pyrazolo[4,3-d]pyrimidine-3-yl]-1-piperidinecarboxylate and 1-methylindole carbonyl chloride in the manner described for the preparation of N2-{4-[7-amino-3-(4-piperidyl)-1H-pyrazolo[4,3-d]pyrimidin-1-yl]-2-methoxyphenyl}-1-methyl-1H-2-indolecarboxamide: $^1$H NMR (DMSO-d$_6$, 400 MHz) δ 10.85 (s, 1H), 8.28 (s, 1H), 8.03 (d, 2H), 7.74 (d, 1H), 7.58 (d, 1H), 7.53 (d, 2H), 7.37 (s, 1H), 7.34 (t, 114), 7.15 (t, 1H), 6.5 (bs, 1.4H), 4.04 (s, 3H), 3.19 (m, 1H), 3.10 (m, 2H), 2.70 (m, 2H), 1.84-2.0 (m, 4H); RP-HPLC (Hypersil HS C18, 5 μm, 100 A, 250×4.6 mm; 5%-100% acetonitrile-0.05 M ammonium acetate over 25 min, 1 mL/min) $t_r$ 14.42 min; MS: MH$^+$ 467.1, M–H$^+$ 465.1

Example 12

N2-{4-[7-Amino-3-(1,2,3,6-tetrahydro-4-pyridinyl)-1H-pyrazolo[4,3-d]pyrimidin-1-yl]-2-methoxyphenyl}-1-methyl-1H-2-indolecarboxamide bisacetate The title compound was prepared by hydrogenation of a methanolic solution of tert-butyl 4-[7-amino-1-(3-methoxy-4-nitrophenyl)-1H-pyrazolo[4,3-d]pyrimidin-3-yl]-1,2,3,6-tetrahydro-1-pyridinecarboxylate in the presence of 10% Pd—C at 55 psi of hydrogen for 12 hours to provide tert-butyl 4-[7-amino-1-(4-amino-3-methoxyphenyl)-1H-pyrazolo[4, 3-d]pyrimidine-3-yl]-1,2,3,6-tetrahydro-1-pyridinecarboxylate which was then reacted with 1-Methylindole carbonyl chloride in the manner described for the preparation of N2-{4-[7-amino-3-(4-piperidyl)-1H-pyrazolo[4,3-d]pyrimidin-1-yl]-2-methoxyphenyl}-1-methyl-1H-2-indolecarboxamide: $^1$H NMR (DMSO-d$_6$, 400 MHz) δ 9.49 (bs, 1H), 8.35 (s, 1H), 8.12 (d, 1H), 7.71 (d, 1H), 7.60 (m, 1H), 7.46 (s, 1H), 7.32 (m, 3H), 7.16 (m, 2H), 4.04 (s, 3H), 3.94 (s, 3H), 3.50 (m, 2H), 2.96 (m, 2H), 2.54 (m, 2H), 1.88 (s, 6H); RP-HPLC (Hypersil HS C18, 5 μm, 100 A, 250×4.6 mm; 5%-100% acetonitrile-0.05 M ammonium acetate over 25 min, 1 mL/min) t$_r$ 15.42 min; MS: MH$^+$ 495.2, M−H$^+$ 493.3

Example 13

N-[4-(4-Aminofuro[2,3-d]pyrimidin-5-yl)phenyl]-N'-(4-methylphenyl)urea

Example 13A

2-Hydroxy-1-(4-nitrophenyl)ethanone

A mixture of 2-bromo-1-(4-nitrophenyl)ethanone (5 g, 20.5 mmol) and silver nitrate (5 g, 29.4 mmol) in water (250 mL) and acetone (150 mL) was heated to reflux for 4 hours then cooled to room temperature. The suspension was filtered and the filtrate was extracted twice with dichloromethane. The combined extracts were dried (Na$_2$SO$_4$), filtered, and concentrated. The concentrate was purified by flash column chromatography on silica gel with 2:1 hexanes/ethyl acetate to provide 3.7 g (50%) of the desired product. R$_f$=0.4 (1:1 hexanes/ethyl acetate).

Example 13B

2-Amino-4-(4-nitrophenyl)-3-furonitrile

A mixture of Example 13A (5 g, 27.6 mmol) and malononitrile (2.74 g, 41.4 mmol) in methanol (8.6 mL) at room temperature was treated with diethylamine (1.43 mL, 13.8 mmol), stirred for 1 hour, and poured into water. The resulting suspension was filtered and the filter cake was washed with water then purified by flash column chromatography on silica gel with 1:1 ethyl acetate/hexanes to provide 5 g (80%) of the desired product. MS (DCI) m/e 247 (M+NH$_4$)$^+$.

Example 13C

N'-[3-Cyano-4-(4-nitrophenyl)-2-furyl]imidoformamide

A mixture of Example 13B (2 g, 8.7 mmol) and ammonium sulfate (115 mg, 0.87 mmol) in triethylformate (40 mL) was heated to reflux for 4 hours, cooled to −20° C., treated with 2M ammonia in ethanol (80 mL, 160 mmol), warmed to room temperature, and stirred for 5 hours. The resulting precipitate was collected by vacuum filtration, washed with water and ethanol, and dried to provide 2.2 g (98%) of the desired product. MS (ESI(−)) m/e 255 (M−H)$^−$.

Example 13D 5-(4-Nitrophenyl)furo[2,3-d]pyrimidin-4-amine

A suspension of Example 13C (120 mg, 0.47 mmol) in 1,2-dichlorobenzene (5 mL) was heated in a Smith Synthesizer microwave at 250° C. for 15 minutes, diluted with THF, and concentrated. The concentrate was purified by flash column chromatography on silica gel with 5% methanol/dichloromethane to provide 98 mg (82%) of the desired product. MS (ESI(−)) m/e 255 (M−H); $^1$H NMR (DMSO-d$_6$) δ 8.37-8.33 (m, 2H), 8.29 (s, 2H), 8.19 (s, 1H), 7.80-7.75 (m, 2H), 6.80 (br s, 2H); Anal. Calcd. for C$_{12}$H$_8$N$_4$O$_3$: C, 56.25; H, 3.15; N, 21.87. Found: C, 56.32; H, 3.17; N, 21.86.

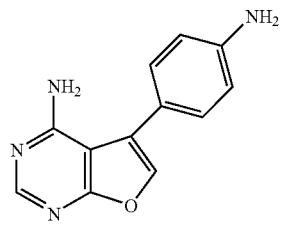

Example 13E 5-(4-Aminophenyl)furo[2,3-d]pyrimidin-4-amine

A mixture of Example 13D (140 mg, 0.55 mmol) and NH$_4$Cl (30 mg, 0.55 mmol) in 2:1 ethanol/water (9 mL) was heated to 50° C., treated with iron powder (61 mg, 1.1 mmol), heated to 80° C. for 2 hours, cooled to room temperature, filtered through diatomaceous earth (Celite®), and concentrated. The concentrate was purified by flash column chromatography on silica gel with 2:1 hexanes/ethyl acetate to provide 95 mg (77%) of the desired product. MS (ESI(+)) m/e 227 (M+H)$^+$.

Example 13F

N-[4-(4-Aminofuro[2,3-d]pyrimidin-5-yl)phenyl]-N'-(4-methylphenyl)urea

A 0° C. suspension of Example 13E (50 mg, 0.22 mmol) in dichloromethane (3 mL) was treated with p-tolylisocyanate (0.031 mL, 0.24 mmol), warmed to room temperature, and stirred overnight. The resulting precipitate was collected by vacuum filtration, washed with dichloromethane, and dried to provide 55 mg (70%) of the desired product. MS (ESI(+)) m/e 360 (M+H)$^+$; $^1$H NMR (DMSO-d$_6$) δ 8.80 (s, 1H), 8.60 (s, 1H), 8.25 (s, 1H), 7.92 (s, 1H), 7.6 (d, J=8.4 Hz, 2H), 7.43 (d, J=8.7 Hz, 2H), 7.35 (d, J=8.4 Hz, 2H), 7.10 (d, J=8.1 Hz, 2H), 6.52 (br s, 2H), 2.25 (s, 3H); Anal. Calcd. for C$_{20}$H$_{17}$N$_5$O$_2$: C, 66.84; H, 4.77; N, 19.49. Found: C, 66.58; H, 4.65; N, 19.42.

Example 14

N-[4-(4-aminofuro[2,3-d]pyrimidin-5-yl)phenyl]-N'-(3-methylphenyl)urea

The desired product was prepared by substituting m-tolylisocyanate for p-tolylisocyanate in Example 13F. MS (ESI (+)) m/e 360 (M+H)$^+$; $^1$H NMR (DMSO-d$_6$) δ 8.84 (s, 1H), 8.65 (s, 1H), 8.25 (s, 1H), 7.93 (s, 1H), 7.62-7.59 (m, 2H), 7.45-7.42 (m, 2H), 7.31 (br s, 1H), 7.25 (d, J=8.1 Hz, 1H), 7.17 (t, J=7.2 Hz, 1H), 6.80 (d, J=7.2 Hz, 1H), 6.54 (br s, 2H), 2.28 (s, 3H); Anal. Calcd. for $C_{20}H_{17}N_5O_2 \cdot 0.25H_2O$: C, 66.00; H, 4.85; N, 19.25. Found: C, 66.15; H, 4.68; N, 19.31.

Example 15

N-[4-(4-Aminofuro[2,3-d]pyrimidin-5-yl)phenyl]-N'-(2-methylphenyl)urea

The desired product was prepared by substituting o-tolylisocyanate for p-tolylisocyanate in Example 13F. MS (ESI (+)) m/e 360 (M+H)$^+$; $^1$H NMR (DMSO-d$_6$) δ 9.19 (s, 1H), 8.25 (s, 1H), 7.98 (s, 1H), 7.92 (s, 1H), 7.84 (d, J=7.8 Hz, 1H), 7.62 (d, J=8.7 Hz, 2H), 7.44 (d, J=9.0 Hz, 2H), 7.20-7.13 (m, 2H), 6.96 (dt, J=7.4, 0.9 Hz, 1H), 6.52 (br s, 2H), 2.26 (s, 3H); Anal. Calcd. for $C_{20}H_{17}N_5O_2 \cdot 0.25H_2O$: C, 66.01; H, 4.85; N, 19.25. Found: C, 65.907; H, 4.74; N, 18.98.

Example 16

N-[4-(4-Aminofuro[2,3-d]pyrimidin-5-yl)phenyl]-N'-(3 chlorophenyl)urea

The desired product was prepared by substituting 3-chlorophenylisocyanate for p-tolylisocyanate in Example 13F. MS (ESI(+)) m/e 378, 380 (M+H)$^+$; $^1$H NMR (DMSO-d$_6$) δ 8.94 (s, 2H), 8.25 (s, 1H), 7.93 (s, 1H), 7.73-7.72 (m 1H), 7.61 (d, J=8.4 Hz, 2H), 7.44 (d, J=8.4 Hz, 2H), 7.32-7.29 (m, 2H), 7.03 (dt, J=6.5, 2.2 Hz, 1H); Anal. Calcd. for $C_{19}H_{14}ClN_5O_2 \cdot 0.25H_2O$: C, 59.38; H, 3.80; N, 18.22. Found: C, 59.42; H, 3.80; N, 18.12.

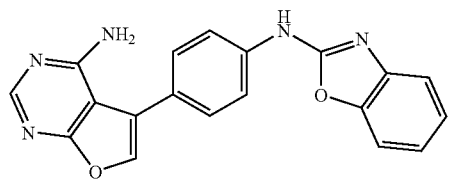

Example 17

5-[4-(1,3-Benzoxazol-2-ylamino)phenyl]furo[2,3-d]pyrimidin-4-amine

A solution of Example 13E (80 mg, 0.35 mmol) in pyridine (3 mL) was added dropwise via cannula to a 0° C. solution of 1,1-thiocarbonyldiimidazole (63 mg, 0.35 mmol) in pyridine (3 mL). The reaction was stirred at 0° C. for 1.5 hours, treated with 2-aminophenol (393 mg, 0.359 mmol), warmed to room temperature, stirred overnight, treated with 1-ethyl-3-(3-dimethylaminopropyl)carbodiimide hydrochloride (81 mg, 0.42 mmol), and heated to 55° C. for 8 hours. The mixture was concentrated and the residue was partitioned between ethyl acetate and water. The aqueous phase was extracted three times with ethyl acetate and the combined extracts were washed with brine, dried (Na$_2$SO$_4$), filtered, and concentrated. The concentrate was purified by flash column chromatography on silica gel with ethyl acetate to provide 31 mg (25%) of the desired product. MS (ESI(+)) m/e 344 (M+H)$^+$; $^1$H NMR (DMSO-d$_6$) δ 10.82 (s, 1H), 2.56 (s, 1H), 7.94 (s, 1H), 7.93-7.89 (m, 2H), 7.56-7.48 (m, 4H), 7.24 (dt, J=7.2, 1.2 Hz, 1H), 7.15 (dt, J=7.8, 1.2 Hz, 1H), 6.54 (br s, 2H). Anal. Calcd. for $C_{18}H_{13}N_5O_2 \cdot 0.25H_2O$: C, 65.61; H, 3.91; N, 20.13. Found: C, 65.75; H, 3.96; N, 19.78.

Example 18

N-[4-(4-Aminofuro[2,3-d]primidin-5-yl)phenyl]benzamide

A 0° C. suspension of Example 13E (74 mg, 0.33 mmol) in dichloromethane (3 mL) was treated with pyridine (0.032 mL, 0.4 mmol) and benzoyl chloride (0.040 mL, 0.34 mmol), stirred at 0° C. for 1 hour, warmed to room temperature, and stirred overnight. The mixture was triturated with hexanes and the precipitate was collected by vacuum filtration, washed with dichloromethane and water, and purified by flash column chromatography on silica gel with ethyl acetate to provide 46 mg (42%) of the desired product. MS (ESI(+)) m/e 331 (M+H)$^+$; $^1$H NMR (DMSO-d$_6$) δ 10.41 (s, 1H), 8.26 (s, 1H), 7.99-7.94 (m, 5H), 7.62-7.50 (m, 5H), 6.50 (br s, 2H); Anal. Calcd. for $C_{19}H_{14}N_4O_2 \cdot 0.25H_2O$: C, 68.15; H, 4.36; N, 16.73. Found: C, 68.20; H, 4.21; N, 19.78.

Example 19

N-[4-(4-Aminofuro[2,3-d]pyrimidin-5-yl)phenyl]benzenesulfonamide

A 0° C. suspension of Example 13E (0.05 g, 0.22 mmol) in dichloromethane (4 mL) was treated with pyridine (0.022 mL, 0.26 mmol) and benzenesulfonyl chloride (0.03 mL, 0.23 mmol), stirred at 0° C. for 1 hour, warmed to room temperature, and stirred overnight. The reaction mixture was diluted with water and extracted twice with dichloromethane. The combined extracts were washed with brine, dried (Na$_2$SO$_4$), filtered, and concentrated. The concentrate was triturated with dichloromethane/hexanes to provide 52 mg (64%) of the desired product. MS (ESI(+)) m/e 367 (M+H)$^+$; $^1$H NMR (DMSO-d$_6$) δ 10.51 (s, 1H), 8.23 (s, 1H), 7.88 (s, 1H), 7.84-7.81 (m, 2H), 7.64-7.54 (m, 3H), 7.38 (d, J=8.5 Hz, 2H), 7.22 (d, J=8.5 Hz, 2H), 6.45 (br s, 2H); Anal. Calcd. for $C_{18}H_{14}N_4O_3S$: C, 59.01; H, 3.85; N, 15.29. Found: C, 58.77; H, 3.88; N, 15.18.

Example 20

N-[4-(4-Amino-6-methylfuro[2,3-d]pyrimidin-5-yl)phenyl]-N'-(2-methylphenylurea

Example 20A

1-(4-Nitrophenyl)propan-1-one

A solution of 0.5M ZnCl$_2$ in THF (60 mL, 30 mmol) in THF (20 mL) at room temperature was treated with 2M ethyl magnesium chloride in THF (15 mL, 30 mmol) dropwise via syringe, cooled with an ice bath for about 10 minutes, stirred at room temperature for 20 minutes, cooled to 0° C., and treated sequentially with Pd(PPh$_3$)$_4$ (1.73 g, 1.5 mmol) and a solution of 4-nitrobenzoyl chloride (6.12 g, 33 mmol) in THF (20 mL). The mixture was stirred at 0° C. for 40 minutes, diluted with water and extracted three times with ethyl acetate. The combined extracts were washed with saturated Na$_2$CO$_3$, water, and brine, dried (MgSO$_4$), filtered, and concentrated. The concentrate was purified by flash column chromatography on silica gel with 6:1 hexanes/ethyl acetate to provide 2.17 g (40%) of the desired product. $R_f$=0.6 (3:1 hexanes/ethyl acetate).

Example 20B

2-Bromo-1-(4-nitrophenyl)propan-1-one

A solution of bromine (0.805 mL, 15.6 mmol) in $CCl_4$ (10 mL) was added dropwise to a solution of Example 20A (2.8 g, 15.6 mmol) in $CCl_4$ (20 mL) at room temperature, stirred for 1 hour, quenched with 1:1 saturated $NaHCO_3$/10% $NaHSO_3$, and extracted with dichloromethane. The combined extracts were washed with water, dried ($Na_2SO_4$), filtered, and concentrated to provide 3.95 g (98%) of the desired product. $R_f$=0.62 (2:1 hexanes/ethyl acetate).

Example 20C

2-Hydroxy-1-(4-nitrophenyl)propan-1-one

A solution of $LiOH.H_2O$ (642 mg, 15.3 mmol) in water (15 mL) was added dropwise to a 0° C. solution of Example 20B (3.95 g, 15.3 mmol) in DMF (54 mL), stirred at 0° C. for 1 hour, diluted with water, and extracted three times with ethyl acetate. The combined extracts were washed with brine, dried ($Na_2SO_4$), filtered, and concentrated to provide 2.65 (89%) of the desired product. $R_f$=0.27 (2:1 hexanes/ethyl acetate).

Example 20D 5-(4-Aminophenyl)-6-methylfuro[2,3-d]pyrimidin-4-amine

The desired product was prepared by substituting Example 20C for Example 13A in Examples 13B-13E. $^1$H NMR (300 MHz, DMSO-$d_6$) δ 2.33 (s, 3H), 5.33 (s, 2H), 6.13 (br s, 2H), 6.70 (m, 2H), 7.08 (m, 2H), 8.16 (s, 1H); Anal. Calcd. for $C_{13}H_{12}N_4O$: C, 64.99; H, 5.03; N, 23.32. Found: C, 64.67; H, 5.02; N, 23.05.

Example 20E

N-[4-(4-Amino-6-methylfuro[2,3-d]pyrimidin-5-yl) phenyl]-N'-(2-methylphenyl)urea The desired product was by substituting Example 20D and o-tolylisocyanate for Example 13E and p-tolylisocyanate, respectively, in Example 13F. $^1$H NMR (500 MHz, DMSO-$d_6$) δ 2.26 (s, 3H), 2.37 (s, 3H), 6.18 (br s, 2H), 6.97 (t, J=7.5 Hz, 1H), 7.16 (t, J=7.8 Hz, 1H), 7.19 (d, J=7.5 Hz, 1H), 7.36 (d, J=8.4 Hz, 2H), 7.63 (d, J=8.4 Hz, 2H), 7.83 (d, J=7.8 Hz, 1H), 7.98 (s, 1H), 8.19 (s, 1H), 9.17 (s, 1H); Anal. Calcd. for $C_{21}H_{19}N_5O_2.0.25H_2O$: C, 66.74; H, 5.20; N, 18.53. Found: C, 66.63; H, 4.90; N, 18.55.

Example 21

N-[4-(4-Amino-6-methylfuro[2,3-d]pyrimidin-5-yl) phenyl]-N'-(4-methylphenyl)urea The desired product was prepared by substituting Example 20D for Example 13E in Example 13F. $^1$H NMR (500 MHz, DMSO-$d_6$) δ 2.25 (s, 3H), 2.37 (s, 3H), 6.18 (br s, 2H), 7.10 (d, J=8.4 Hz, 2H), 7.35 (m, 4H), 7.61 (d, J=8.4 Hz, 2H), 8.19 (s, 1H), 8.59 (s, 1H), 8.78 (s, 1H); Anal. Calcd. for $C_{21}H_{19}N_5O_2.0.4H_2O$: C, 66.27; H, 5.24; N, 18.40. Found: C, 65.84; H, 4.80; N, 18.07.

Example 22

N-[4-(4-Amino-6-methylfuro[2,3-d]pyridin-5-yl) phenyl]benzamide

The desired product was prepared by substituting Example 20D for Example 13E in Example 18. MS (DCI) m/e 345 (M+H)$^+$; $^1$H NMR (300 MHz, DMSO-$d_6$) δ 2.39 (s, 3H), 6.23 (br s, 2H), 7.43 (m, 2H), 7.59 (m, 3H), 7.96 (m, 2H), 7.98 (m, 2H), 8.20 (s, 1H), 10.42 (s, 1H); Anal. Calcd. for $C_{20}H_{16}N_4O_{22}.0.5H_2O$: C, 67.98; H, 4.85; N, 15.85. Found: C, 67.83; H, 4.73; N, 15.61.

Example 23

N-[4-(4-Amino-6-methylfuro[2,3-d]pyrimidin-5-yl) phenyl]benzenesulfonamide

The desired product was prepared by substituting Example 20D for Example 13E in Example 19. MS (DCI) m/e 381 (M+H)$^+$; $^1$H NMR (300 MHz, DMSO-$d_6$) δ 2.30 (s, 3H), 6.16 (br s, 2H), 7.24 (d, J=8.4 Hz, 2H), 7.30 (d, J=8.4 Hz, 2H), 7.57 (t, J=7.6 Hz, 2H), 7.64 (t, J=7.3 Hz, 1H), 7.80 (d, J=7.2 Hz, 2H), 8.19 (s, 1H), 10.49 (s, 1H); Anal. Calcd. for $C_{19}H_{16}N_4O_3S1.0H_2O$: C, 57.28; H, 4.55; N, 14.06. Found: C, 57.67, H, 4.13; N, 14.04.

Example 24

N-[4-(4-Amino-6-methylfuro[2,3-d]pyrimidin-5-yl) phenyl]-N'-(3-methylphenyl)urea The desired product was prepared by substituting Example 20D and m-tolylisocyanate for Example 13E and p-tolylisocyanate, respectively, in Example 13F. MS (DCI) m/e 374 (M+H)$^+$; $^1$H NMR (300 MHz, DMSO-$d_6$) δ 2.29 (s, 3H), 2.37 (s, 3H), 6.22 (br s, 2H), 6.80 (d, J=7.1 Hz, 1H), 7.17 (t, J=7.6 Hz, 1H), 7.31 (m, 1H), 7.35 (d, J=8.5 Hz, 2H), 7.62 (d, J=8.8 Hz, 2H), 8.19 (s, 1H), 8.65 (s, 1H), 8.83 (s, 1H); Anal. Calcd. for $C_{21}H_{19}N_5O_2$: C, 67.55; H, 5.13; N, 18.75. Found: C, 67.32; H, 5.11; N, 18.70.

Example 25

N-[4-(4-Amino-6-methylfuro[2,3-d]pyrimidin-5-yl) phenyl]-N'-(3-chlorophenyl)urea The desired product was prepared by substituting Example 20D and 3-chlorophenylisocyanate for Example 13E and p-tolylisocyanate, respectively, in Example 13F. MS (DCI) m/e 394 (M+H)$^+$; $^1$H NMR (300 MHz, DMSO-$d_6$) δ 2.37 (s, 3H), 6.21 (br s, 2H), 7.03 (dt, J=6.4, 2.0 Hz, 1H), 7.31 (m, 2H), 7.36 (d, J=8.5 Hz, 2H), 7.62 (d, J=8.8 Hz, 2H), 7.73 (m, 1H), 8.19 (s, 1H), 8.93 (s, 1H), 8.94 (s, 1H); Anal. Calcd. for $C_{20}H_{16}ClN_5O_2.0.35H_2O$: C, 60.03; H, 4.21; N, 17.50. Found: C, 60.51; H, 3.88; N, 17.02.

Example 26

N-[4-(4-Amino-6-methylfuro[2,3-d]pyrimidin-5-yl) phenyl]-N'-(3-methoxyphenyl)urea The desired product was prepared by substituting Example 20D and 3-methoxyphenylisocyanate for Example 13E and p-tolyisocyanate, respectively, in Example 13F. MS (DCI) m/e 390 (M+H)$^+$; $^1$H NMR (300 MHz, DMSO-$d_6$) δ 2.37 (s, 3H), 3.74 (s, 3H), 6.21 (br s, 2H), 6.56 (m, 1H), 6.95 (m, 1H), 7.18 (s, 1H), 7.20 (m, 1H), 7.35 (d, J=8.5 Hz, 2H), 7.62 (d, J=8.5 Hz, 2H), 8.19 (s, 1H), 8.73 (s, 1H), 8.83 (s, 1H); Anal. Calcd. for $C_{21}H_{19}N_5O_3$: C, 64.77; H, 4.92; N, 17.98. Found: C, 64.41; H, 4.83; N, 17.71.

Example 27

N-[4-(4-Amino-6-bromofuro[2,3-d]pyrimidin-5-yl)phenyl]-N"-(3-methylphenyl)urea

Example 27A tert-Butyl 5-(4-nitrophenyl)furo[2,3-d]pyrimidin-4-ylcarbamate

A 0° C. suspension of Example 13D (0.44 g, 1.7 mmol) in THF (20 mL) was treated with 60% NaH oil dispersion (172 mg, 4.25 mmol), stirred at 0° C. for 15 minutes, treated with di-t-butyl dicarbonate (450 mg, 2.04 mmol), stirred at 0° C. for 1 hour, and quenched with saturated $NH_4Cl$. The mixture was extracted three times with ethyl acetate and the combined extracts were washed with water and brine, dried ($Na_2SO_4$), filtered, and concentrated. The concentrate was purified by flash column chromatography on silica gel with 2:1 hexanes/ethyl acetate to provide 550 mg (89%) of the desired product. MS (ESI(+)) m/e 357 $(M+H)^+$.

Example 27B tert-Butyl 6-bromo-5-(4-nitrophenyl)furo[23-d]pyrimidin-4-ylcarbamate A 0° C. solution of Example 27A (350 mg, 0.98 mmol) in DMF (10 mL) was treated with $Br_2$ (0.102 mL, 1.98 mmol), warmed to room temperature, and stirred for 1 hour. The reaction was cooled to 0° C., quenched with 1:1 10% $NaHSO_3$/saturated $NaHCO_3$, and extracted three times with ethyl acetate. The combined extracts were washed with water and brine, dried ($Na_2SO_4$), filtered, and concentrated to provide 400 mg (93%) of the desired product. MS (ESI(−)) m/e 433, 435 $(M-H)^-$.

Example 27C tert-Butyl 6-bromo-5-[4-({[(3-methylphenyl)amino]carbonyl}amino)phenyl]furo[2,3-d]pyrimidin-4-ylcarbamate The desired product was prepared by substituting Example 27B and m-tolylisocyanate for Example 13D and p-tolylisocyanate, respectively, in Examples 13E and 13F. MS (ESI(−)) m/e 536, 538 $(M-H)^-$.

Example 27D

N-[4-(4-Amino-6-bromofuro[2,3]pyrimidin-5-yl)phenyl]-N'-(3-methylphenyl)urea

A 0° C. suspension of Example 27C (94 mg, 0.17 mmol) in dichloromethane (4 mL) was treated with TFA (1 mL), warmed to room temperature, stirred for 1 hour, and concentrated. The concentrate was purified by flash column chromatography with 5% methanol/dichloromethane to provide 64 mg (88%) of the desired product. MS (ESI(+)) m/e 438, 440 $(M+H)^+$; $^1$H NMR (DMSO-$d_6$) δ 8.88 (s, 1H), 8.66 (s, 1H), 8.24 (s, 1H), 7.64 (d, J=8.4 Hz, 2H), 7.41 (d, J=8.7 Hz, 2H), 7.32 (br s, 1H), 7.25 (d, J=8.7 Hz, 1H), 7.17 (t, J=7.6 Hz, 1H), 6.81 (d, J=7.8 Hz, 1H), 6.48 (br s, 2H), 2.29 (s, 3H); Anal. Calcd. for $C_{20}H_{16}N_5O_2Br.H_2O$: C, 52.65; H, 3.98; N, 15.35. Found: C, 52.50; H, 3.77; N, 15.10.

Example 28

N-[4-(4-Amino-6-methylfuro[2,3-d]pyrimidin-5-yl)phenyl]-N'-(3-bromophenyl)urea

Example 28A

6-Methyl-5-(4-nitrophenyl)furo[2,3-d]pyrimidin-4-amine

The desired product was prepared by substituting Example 20C for Example 13A in Examples 13B-13D.

Example 28B tert-Butyl 6-methyl-5-(4-nitrophenyl)furo[2,3-d]pyrimidin-4-ylcarbamate The desired product was prepared by substituting Example 28A for Example 13D in Example 27A.

Example 28C tert-Butyl 5-[4-({[(3-bromophenyl)amino]carbonyl}amino)phenyl]-6-methylfuro[2,3-d]pyrimidin-4-ylcarbamate The desired product was prepared by substituting Example 28B and 3-bromophenylisocyanate for Example 13D and p-tolylisocyanate, respectively, in Examples 13E and 13F.

Example 28D

N-[4-(4-Amino-6-methylfuro[2,3-d]pyrimidin-5-yl)phenyl]-N'-(3-bromophenyl)urea

The desired product was prepared by substituting Example 28C for Example 27C in Example 27D. $^1$H NMR (300 MHz, DMSO-$d_6$) δ 2.40 (s, 3H), 5.93 (br s, 2H), 7.16 (m, 1H), 7.25 (t, J=7.98 Hz, 1H), 7.36 (m, 3H), 7.65 (m, 2H), 7.89 (t, J=1.84 Hz, 1H), 8.34 (s, 1H), 9.11 (s, 1H), 9.12 (s, 1H); Anal. Calcd. for $C_{20}H_{16}BrN_5O_2.1.4CF_3CO_2H$: C, 44.23; H, 3.02; N, 12.05. Found: C, 44.42; H, 3.03; N, 11.79.

Example 29

3-(4-Nitrophenyl)isoxazolo[5,4-d]primidin-4-amine

Example 29A

5-Amino-3-(4-nitrophenyl)isoxazole-4-carbonitrile

A mixture of 0.5M sodium methoxide in methanol (62.8 mL, 31.4 mmol) and malononitrile (2.07 g, 31.4 mmol) was stirred at 0° C. for 10 minutes then treated dropwise with solution of N-[(Z)-2-chloro-2-(4-nitrophenyl)vinyl]hydroxylamine (prepared according to the procedure described in U.S. Pat. No. 5,567,843, 6.3 g, 31.4 mmol) in THF (30 mL), warmed to room temperature, and stirred for two hours. The mixture was diluted with water (500 mL) and filtered. The filter cake was washed with water and hexanes and dried to provide 5.4 g (75% yield) of the desired product. MS (ESI(−)) m/e 229 $(M-H)^-$.

Example 29B 3-(4-Nitrophenyl)isoxazolo[5,4-d]pyrimidin-4-amine

A mixture of Example 29A (3.0 g, 13 mmol), $(NH_4)_2SO_4$ (172 mg, 1.3 mmol), and $HC(OCH_2CH_3)_3$ (105 mL) was heated to reflux for 6 hours, then filtered while hot. The filtrate was treated with saturated $NH_3$ in ethanol (150 mL), stirred overnight at room temperature, and filtered. The filter cake was washed with ethanol and dried to provide 1.84 g (55% yield) of the desired product.

Example 30

3-(4-Aminophenyl)isoxazolo[5,4-d]pyrimidin-4-amine

A 0° C. suspension of Example 29B (124 mg, 0.5 mmol) in concentrated HCl (2 mL) was treated with a solution of $SnCl_2$ (450 mg) in concentrated HCl (1 mL), warmed to room temperature, stirred for 3 hours, and filtered. The filtrate was partitioned between ethyl acetate and saturated $NaHCO_3$ and the organic phase was washed with brine, dried ($MgSO_4$), filtered, and concentrated to provide 37 mg (32%) of the desired product. MS (ESI(−)) m/e 226 (M−H)⁻.

Example 31

N-[4-(4-Aminoisoxazolo[5,4-d]pyrimidin-3-yl)phenyl]-N-(3-methylphenyl)urea

A 0° C. solution of Example 30 (126 mg, 0.3 mmol) in DMF (2 mL) at room temperature was treated with pyridine (0.121 mL, 1.5 mmol) and 3-methylphenylisocyanate (0.038 mL, 0.3 mmol) and stirred overnight. The reaction mixture was poured into ice water and filtered. The filter cake was recrystallized from ethyl acetate/hexanes to provide 87 mg (80% yield) of the desired product. MS (ESI(+)) m/e 361 (M+H)⁺; ¹H NMR (DMSO-$d_6$) δ 9.00 (s, 1H), 8.69 (s, 1H), 8.42 (s, 1H), 7.68 (q, J=15, 8.7 Hz, 4H), 7.10-7.40 (m, 3H), 6.82 (d, J=7.2 Hz, 1H), 2.28 (s, 3H).

Example 32

N-[4-(4-Aminoisoxazolo[5,4-d]pyrimidin-3-yl)phenyl]-N'-(3-ethylphenyl)urea

The desired product was prepared by substituting 3-ethylphenylisocyanate for m-tolylisocyanate in Example 31. ¹H NMR (DMSO-$d_6$) δ 9.00 (s, 1H), 8.87 (s, 1H), 8.42 (s, 1H), 7.66 (q, J=15, 8.7 Hz, 4H), 7.10-7.40 (m, 3H), 6.83 (d, J=7.2 Hz, 1H), 2.59 (q, J=7.5 Hz, 2H), 1.20 (t, J=7.5 Hz, 3H).

Example 33

N-[4-(4-aminoisoxazolo[5,4-d]pyrimidin-3-yl)phenyl]-N'-(3-chlorophenyl)urea

The desired product was prepared by substituting 3-chlorophenylisocyanate for m-tolylisocyanate in Example 31. MS (ESI(+)) m/e 380 (M+H)⁺; ¹H NMR (DMSO-$d_6$) δ 9.07 (s, 1H), 9.00 (s, 1H), 8.42 (s, 1H), 7.60-7.80 (m, 5H), 7.20-7.40 (m, 2H), 6.90-7.10 (m, 1H).

Example 34

N-[4-(4-Aminoisoxazolo[5,4-d]pyridin-3-yl)phenyl]benzamide

The desired product was prepared by substituting Example 20 for Example 13E in Example 18. MS (ESI(+)) m/e 332 (M+H)⁺; ¹H NMR (DMSO-$d_6$) δ 10.48 (s, 1H), 8.42 (s, 1H), 7.90-8.10 (m, 4H), 7.50-7.80 (m, 5H).

Example 35

N-[4-(4-Amino-6-methylfuro[2,3-d]pyrimidin-5-yl)phenyl]-N'-(3-ethylphenyl)urea

The desired product was prepared by substituting Example 20D and 3-ethylphenylisocyanate for Example 13E and p-tolylisocyanate, respectively, in Example 13F. ¹H NMR (500 MHz, DMSO-$d_6$) δ 1.19 (t, J=7.7 Hz, 3H), 2.37 (s, 3H), 2.59 (q, J=7.6 Hz, 2H), 6.19 (br s, 2H), 6.84 (d, J=7.5 Hz, 1H), 7.19 (t, J=7.8 Hz, 1H), 7.27 (d, J=8.1 Hz, 1H), 7.34 (m, 1H), 7.35 (m, 2H), 7.62 (m, 2H), 8.19 (s, 1H), 8.64 (s, 1H), 8.80 (s, 1H); Anal. Calcd. for $C_{22}H_{21}N_5O_2 \cdot 0.25H_2O$: C, 67.42; H, 5.53; N, 17.87. Found: C, 67.48; H, 5.24; N, 18.17.

Example 36

N-[4-(4-Amino-6-methylfuro[2,3-d]pyrimidin-5-yl)phenyl]-N'-(3,5-dimethylphenyl)urea The desired product was prepared by substituting Example 20D and 3,5-dimethylphenylisocyanate for Example 13E and p-tolylisocyanate, respectively, in Example 13F. MS (DCI) m/e 388 (M+H)⁺; ¹H NMR (500 MHz, DMSO-$d_6$) δ 2.27 (s, 6H), 2.37 (s, 3H), 6.18 (br s, 2H), 6.63 (s, 1H), 7.09 (s, 2H), 7.35 (d, J=8.4 Hz, 2H), 7.61 (d, J=8.4 Hz, 2H), 8.19 (s, 1H), 8.54 (s, 1H), 8.79 (s, 1H); Anal. Calcd. for $C_{22}H_{21}N_5O_2 \cdot 0.25H_2O$: C, 67.42; H, 5.53; N, 17.87. Found: C, 67.13; H, 5.20; N, 17.96.

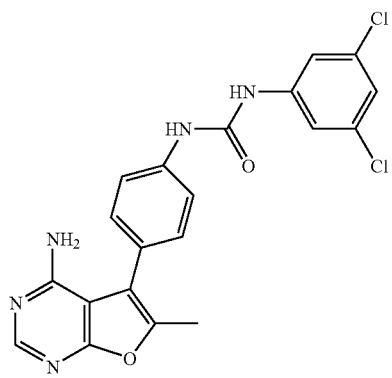

Example 37

N-[4-(4-Amino-6-methylfuro[2,3-d]pyrimidin-5-yl)phenyl]-N'-(3,5-dichlorophenyl)urea The desired product was prepared by substituting Example 20D and 3,5-dichlorophenylisocyanate for Example 13E and p-tolylisocyanate, respectively, in Example 13F. ¹H NMR (500 MHz, DMSO-$d_6$) δ 2.37 (s, 3H), 6.19 (br s, 2H), 7.17 (s, 1H), 7.38 (d, J=8.4 Hz, 2H), 7.56 (s, 2H), 7.63 (d, J=8.4 Hz, 2H), 8.19 (s, 1H), 9.04 (s, 1H), 9.10 (s, 1H); Anal. Calcd. for

Example 38

N-[4-(4-Amino-6-methylfuro[2,3-d]pyrimidin-5-yl)phenyl]-N-[2-fluoro-5-(trifluoromethyl)phenyl]urea The desired product was prepared by substituting Example 20D and 2-fluoro-5-trifluoromethylphenylisocyanate for Example 13E and p-tolylisocyanate, respectively, in Example 13F. MS (DCI) m/e 446 (M+H)$^+$; $^1$H NMR (500 MHz, DMSO-d$_6$) δ 2.38 (s, 3H), 6.20 (br s, 2H), 7.38-7.42 (m, 3H), 7.51 (m, 1H), 7.64 (d, J=8.4 Hz, 2H), 8.19 (s, 1H), 8.64 (dd, J=2.2, 7.2 Hz, 1H), 8.95 (d, J=2.5 Hz, 1H), 9.34 (s, 1H); Anal. Calcd. for C$_{21}$H$_{15}$F$_4$N$_5$O$_2$.0.25H$_2$O: C, 56.07; H, 3.47; N, 15.57. Found: C, 55.89; H, 3.20; N, 15.80.

Example 39

1-[4-(4-Amino-6-methyl-furo[2,3-d]pyrimidin-5-yl)-phenyl]3-(4-cyano-phenyl)-urea The desired product was prepared by substituting Example 20D and 4-cyanophenylisocyanate for Example 13E and p-tolylisocyanate, respectively, in Example 13F. MS (DCI) m/e 385 (M+H)$^+$; $^1$H NMR (500 MHz, DMSO-d$_6$) δ 2.37 (s, 3H), 6.19 (br s, 2H), 7.38 (d, J=8.73 Hz, 2H), 7.63 (d, J=8.73 Hz, 2H), 7.66 (d, J=8.73 Hz, 2H), 7.74 (d, J=8.73 Hz, 2H), 8.19 (s, 1H), 9.03 (s, 1H), 9.25 (s, 1H); Anal. Calcd. for C$_{21}$H$_{16}$N$_6$O$_2$.0.5CH$_2$Cl$_2$: C, 60.50; H, 4.01; N, 19.69. Found: C, 60.15; H, 4.28; N, 19.75.

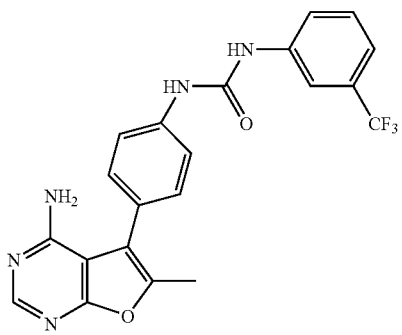

Example 40

1-[4-(4-Amino-6-methyl-furo[2,3-d]pyrimidin-5-yl)-phenyl]-3-(3-trifluoromethyl-phenyl)-urea The desired product was prepared by substituting Example 20D and 3-trifluoromethylphenylisocyanate for Example 13E and p-tolylisocyanate, respectively, in Example 13F. MS (ESI) m/e 428 (M+H)$^+$; $^1$H NMR (500 MHz, DMSO-d$_6$) δ 2.38 (s, 3H), 6.20 (br s, 2H), 7.33 (d, J=7.49 Hz, 1H), 7.37 (d, J=8.11 Hz, 2H), 7.53 (t, J=7.80 Hz, 1H), 7.61 (d, J=8.11 Hz, 1H), 7.64 (d, J=8.11 Hz, 2H), 8.04 (s, 1H), 8.20 (s, 1H), 8.96 (s, 1H), 9.09 (s, 1H); Anal. Calcd. for C$_{21}$H$_{16}$F$_3$N$_5$O$_2$: C, 59.02; H, 3.77; N, 16.39. Found: C, 58.79; H, 3.64; N, 16.23.

Example 41

N-[4-(4-Aminoisoxazolo[5,4-d]pyrimidin-3-yl)phenyl]N'-[3-(trifluoromethyl)phenyl]urea The desired product was prepared by substituting 3-trifluoromethylphenylisocyanate for m-tolylisocyanate in Example 31. MS (ESI(+)) m/e 415.1 (M+H)$^+$; $^1$H NMR (DMSO-d$_6$) δ 9.17 (s, 1H), 8.41 (s, 1H), 8.02 (s, 1H), 7.45-7.80 (m, 7H), 7.35 (d, J=8.4 Hz, 1H).

Example 42

N-[4-(4-Aminoisoxazolo[5,4-d]pyrimidin-3-yl)phenyl]-N'-[2-fluoro-5-(trifluoromethyl)phenyl]urea The desired product was prepared by substituting 2-fluoro-5-trifluoromethylphenyliso-cyanate for m-tolylisocyanate in Example 31. MS (ESI(+)) m/e 433.0 (M+H)$^+$; $^1$H NMR (DMSO-d$_6$) δ 9.50 (s, 1H), 9.00 (d, J=2 Hz, 1H), 8.24 (dd, J=7.2, 2 Hz, 1H), 8.41 (s, 1H), 7.40-7.80 (m, 6H).

What is claimed is:

1. A compound of the formula I,

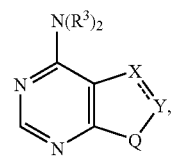

the racemic-diastereomeric mixtures, optical isomers, or pharmaceutically-acceptable salts thereof, wherein the dotted line in the structure of formula (I) represents an optional double bond;

X is CR$^1$; Y is N; Q is O;

R$^3$ for each occurrence is independently hydrogen, hydroxy, substituted or unsubstituted alkyl or substituted or unsubstituted alkoxy;

R$^1$ is

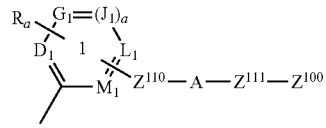

where Z$^{100}$ is nitro, optionally substituted amino,

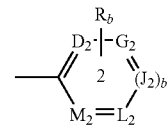

or a group optionally substituted with R$_b$ selected from the group consisting of cycloalkyl, naphthyl, tetrahydronaphthyl, benzothienyl, furanyl, thienyl, benzoxazolyl, benzothiazolyl,

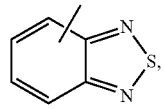 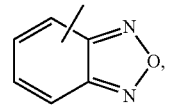

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, oxazolyl, isothiazolyl, oxadiazolyl, thiadiazolyl, indolinyl, indazolyl, benzoisothiazolyl, pyrido-oxazolyl, pyrido-thiazolyl, pyrimido-oxazolyl, pyrimido-thiazolyl and benzimidazolyl;

when a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or when a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N;

when b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or when b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N;

$R_a$ and $R_b$ each represent one or more substituents and are for each occurrence independently selected from the group consisting of hydrogen, halogen, —CN, —NO₂, —C(O)OH, —C(O)H, —OH, —C(O)O-alkyl, —$Z^{105}$—C(O)N(R)₂, —$Z^{105}$—N(R)—C(O)—$Z^{200}$, —$Z^{105}$—N(R)—S(O)₂—$Z^{200}$, —$Z^{105}$—N(R)—C(O)—N(R)—$Z^{200}$, $R_c$, CH₂O$R_e$, tetrazolyl, trifluoromethylcarbonylamino, trifluoromethylsulfonamido, and an optionally substituted group selected from the group consisting of carboxamido, alkyl, alkoxy, aryl, alkenyl, aryloxy, heteroaryloxy, arylalkyl, alkynyl, amino, aminoalkyl, amido groups, heteroarylthio and arylthio;

$Z^{105}$ for each occurrence is independently a covalent bond or ($C_1$-$C_6$) aliphatic;

$Z^{200}$ for each occurrence is independently an optionally substituted ($C_1$-$C_6$) aliphatic, optionally substituted phenyl, or optionally substituted —($C_1$-$C_6$)-phenyl aliphatic group-phenyl;

$R_c$ for each occurrence is independently hydrogen, optionally substituted alkyl, optionally substituted aryl, —CH₂—N$R_d$$R_e$, —W—(CH₂)$_t$—N$R_d$$R_e$, —W—(CH₂)$_t$—Oalkyl, —W—(CH₂)$_t$—S-alkyl or —W—(CH₂)$_t$—OH;

$R_d$ and $R_e$ for each occurrence are independently H, alkyl, alkanoyl or SO₂-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), S(O)₂, or N$R_f$;

$R_f$ for each occurrence is independently H or alkyl;

$Z^{110}$ is a covalent bond, or an optionally substituted ($C_1$-$C_6$) aliphatic which is optionally substituted with one or more substituents selected from the group consisting of alkyl, CN, OH, halogen, NO₂, COOH, optionally substituted amino and optionally substituted phenyl;

$Z^{111}$ is a covalent bond, an optionally substituted ($C_1$-$C_6$) aliphatic or an optionally substituted —(CH₂)$_n$-cycloalkyl-(CH₂)$_n$—; where the optionally substituted groups are optionally substituted with one or more substituents selected from the group consisting of alkyl, CN, OH, halogen, NO₂, COOH, optionally substituted amino and optionally substituted phenyl; or $R^1$ is a substituted or unsubstituted carbocyclic or heterocyclic ring fused with ring 2;

A is a covalent bond, —O—; —S—; —S(O)$_p$—; —N(R)—; —N(C(O)OR)—; —N(C(O)R)—; —N(SO₂R)—; —CH₂O—; —CH₂S—; —CH₂N(R)—; —CH(NR)—; —CH₂N(C(O)R)—; —CH₂N(C(O)OR)—; —CH₂N(SO₂R)—; —CH(NHR)—; —CH(NHC(O)R)—; —CH(NHSO₂R)—; —CH(NHC(O)OR)—; —CH(OC(O)R)—; —CH(OC(O)NHR); —CH=CH—; —C(=NOR)—; —C(O)—; —CH(OR)—; —C(O)N(R)—; —N(R)C(O)—; —N(R)S(O)$_p$—; —OC(O)N(R)—; —N(R)—C(O)—(CH₂), —N(R)—, —N(R)C(O)O—; —N(R)—(CH₂)$_{n+1}$—C(O)—, —S(O)$_p$N(R)—; —N(C(O)R)S(O)$_p$—; —N(R)S(O)$_p$N(R)—; —N(R)—C(O)—(CH₂)$_n$—O—, —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_g$)O—; —N(R)P(OR$_g$)—; —N(R)P(O)(OR$_g$)O—; —N(R)P(O)(OR$_g$)—; —N(C(O)R)P(OR$_g$)O—; —N(C(O)R)P(OR$_g$)—; —N(C(O)R)P(O)(OR$_g$)O—, or —N(C(O)R)P(OR$_g$)—;

p is 1 or 2;

R for each occurrence is independently H, optionally substituted alkyl, optionally substituted arylalkyl or optionally substituted aryl;

$R_g$ for each occurrence is independently H, or an optionally substituted group selected from the group consisting of alkyl, arylalkyl, cycloalkyl and aryl; or R, $R_g$, the nitrogen atom and the phosphorus atom, together form a five- or six-membered heterocyclic ring when R and $R_g$ are in a phosphorus containing group; or A is NRSO₂ and R, $R_a$ and the nitrogen atom together form an optionally substituted five- or six-membered heterocyclic ring fused to ring 1; and n for each occurrence is independently an integer from 0 to 6.

2. A compound according to claim 1 of formula (III),

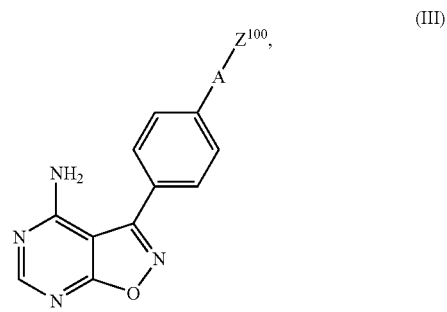

(III)

wherein

A is selected from the group consisting of a covalent bond, —N(R)C(O)—, and —N(R)—C(O)—(CH₂)$_n$—N(R)—;

$Z^{100}$ is selected from the group consisting of nitro, amino, substituted amino, and optionally substituted aryl;

R is hydrogen; and n is 0.

3. The compound of claim 2 wherein

A is a covalent bond; and $Z^{100}$ is selected from the group consisting of nitro, amino and substituted amino.

4. The compound of claim 3 selected from the group consisting of 3-(4-nitrophenyl)isoxazolo[5,4-d]pyrimidin-4-amine; and 3-(4-aminophenyl)isoxazolo[5,4-d]pyrimidin-4-amine.

5. The compound of claim 2 wherein
A is selected from the group consisting of —N(R)C(O)—, and —N(R)—C(O)—$(CH_2)_n$—N(R)—; and $Z^{100}$ is optionally substituted aryl.

6. The compound of claim 5 selected from the group consisting of
N-[4-(4-aminoisoxazolo[5,4-d]pyrimidin-3-yl)phenyl]-N'-(3-methylphenyl)urea;
N-[4-(4-aminoisoxazolo[5,4-d]pyrimidin-3-yl)phenyl]-N'-(3-ethylphenyl)urea;
N-[4-(4-aminoisoxazolo[5,4-d]pyrimidin-3-yl)phenyl]-N'-(3-chlorophenyl)urea;
N-[4-(4-aminoisoxazolo[5,4-d]pyrimidin-3-yl)phenyl] benzamide;
N-[4-(4-aminoisoxazolo[5,4-d]pyrimidin-3-yl)phenyl]-N'-[3-(trifluoromethyl)phenyl]urea; and
N-[4-(4-aminoisoxazolo[5,4-d]pyrimidin-3-yl)phenyl]-N'-[2-fluoro-5-(trifluoromethyl)phenyl]urea.

7. A pharmaceutical composition comprising a compound according to claim 1 and a pharmaceutically acceptable carrier or diluent.

* * * * *

UNITED STATES PATENT AND TRADEMARK OFFICE
CERTIFICATE OF CORRECTION

PATENT NO.       : 7,829,570 B2
APPLICATION NO.  : 12/315416
DATED            : November 9, 2010
INVENTOR(S)      : Gavin C. Hirst et al.

It is certified that error appears in the above-identified patent and that said Letters Patent is hereby corrected as shown below:

Claim 1, Column 69 line 40 delete "-($C_1$-$C_6$)-phenyl aliphatic group-phenyl"
and insert -- -($C_1$-$C_6$) aliphatic group-phenyl --

Claim 1, Column 70 line 14 delete "-N(R)-C(O)-($CH_2$), -N(R)-"
and insert -- -N(R)-C(O)-($CH_2$)$_n$-N(R)- --

Signed and Sealed this
Eighth Day of March, 2011

David J. Kappos
*Director of the United States Patent and Trademark Office*